United States Patent [19]

Fauss et al.

[11] Patent Number: 4,698,333

[45] **Date of Patent: * Oct. 6, 1987**

[54] USE OF SUBSTITUTED MALONIC ACID DERIVATIVES AS AGENTS FOR COMBATING PESTS

[75] Inventors: Rudolf Fauss, Cologne; Reinhard Lantzsch, Leverkusen; Kurt Findeisen, Odenthal; Gerhard Jäger, Leverkusen; Ingeborg Hammann, Muelheim; Benedikt Becker, Mettmann; Bernhard Homeyer, Leverkusen, all of Fed. Rep. of Germany

[73] Assignee: Bayer Aktiengesellschaft, Leverkusen, Fed. Rep. of Germany

[*] Notice: The portion of the term of this patent subsequent to Feb. 7, 2001 has been disclaimed.

[21] Appl. No.: 546,687

[22] Filed: Oct. 28, 1983

[30] Foreign Application Priority Data

Nov. 10, 1982 [DE] Fed. Rep. of Germany ....... 3241512

[51] Int. Cl.[4] ............ A01N 37/20

[52] U.S. Cl. ............ 514/63; 514/517; 514/534; 514/546; 514/595; 514/588; 514/600; 514/601; 514/603; 514/616; 564/48; 564/49; 564/51; 564/59; 564/86; 564/155; 564/158; 564/1; 558/61; 558/62; 556/411; 556/413; 556/419; 556/420; 560/19; 560/85; 560/88; 560/129; 560/155; 560/106; 560/251

[58] Field of Search ............ 514/63, 517, 534, 546, 514/595, 588, 600, 601, 603, 616; 564/158, 48, 49, 51, 58, 59, 86, 153, 154, 155; 556/413, 411, 419, 420; 560/19, 85, 88, 155, 106, 129, 251; 558/62, 61

[56] References Cited

U.S. PATENT DOCUMENTS

| | | | |
|---|---|---|---|
| 3,253,019 | 5/1966 | Davis | 260/484 |
| 3,382,243 | 5/1968 | Bell et al. | 564/158 X |
| 3,707,559 | 12/1977 | Mazur | 564/158 X |
| 4,430,503 | 2/1984 | Findeisen | 556/417 |
| 4,556,649 | 12/1985 | Salzburg et al. | 514/63 |

FOREIGN PATENT DOCUMENTS

| | | | |
|---|---|---|---|
| 0076957 | 4/1983 | European Pat. Off. | 564/158 X |
| 0076985 | 4/1983 | European Pat. Off. | 564/158 X |

OTHER PUBLICATIONS

Monatshefte fur Chemie, vol. 89, 1958, pp. 597–602, Hohenlohe-Oehringen, "Hydrierende Cyclisierung von Azidoverbindungen".

Journal Am. Chem. Soc., vol. 60, May 1938, pp. 1015–1016, J. L. Riebsomer et al, "The Preparation of Substituted Mandelic Acids and Their Bacteriological Effects I".

Chemical Abstracts, vol. 59, 1963, col. 8610, O. Achmatowicz et al, "Monoenic Syntheses".

Chem. Abstracts, vol. 31, 1937, col. 6632, H. Aspelund, "The Action of Alkali on . . . ".

Acta Chemica Scandinavica, vol. 15, 1961, pp. 260–270, S. O. Lawesson et al, "Studies on Peroxy Compounds XI, The Introduction of The t-Butoxy-. . . ".

J. Am. Chem. Soc., vol. 71, 1949, pp. 34–36, C. S. Marvel et al, "Benzoyl Cyanide Dimer and the Addition of Benzoyl Cyanide to Aromatic Aldehydes."

Chemical Abstracts, vol. 52, 1958, col. 11864h, H. Aspelund et al, "1,5-Diphenyl-3-Methyldialuric Acid.

*Primary Examiner*—Paul F. Shaver

*Attorney, Agent, or Firm*—Sprung Horn Kramer & Woods

[57] ABSTRACT

Pesticidally active compounds of the formula

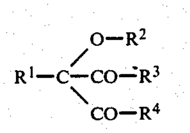

in which $R^1$ is an organic radical, $R^2$ is hydrogen, trialkylsilyl, a hydrocarbon or acyl radical, and $R^3$ and $R^4$ independently are an amino, hydroxyl, hydroximino, alkoxy or like radical.

Most of the compounds are new, as are various intermediates therefor.

8 Claims, No Drawings

USE OF SUBSTITUTED MALONIC ACID DERIVATIVES AS AGENTS FOR COMBATING PESTS

The present invention relates to the use of substituted malonic acid derivatives as agents for combating pests, new substituted malonic acid derivatives and processes for the preparation of the new compounds.

It has already been disclosed that carbamates, such as 5,6-dimethyl-2-dimethylamino-4-pyrimidinyl dimethylcarbamate or 1-naphthyl N-methylcarbamate, have an insecticidal activity (U.S. Pat. Nos. 3,493,574 and 2,903,478). Their action is not always satisfactory when low concentrations are applied.

It has been found that the substituted malonic acid derivatives of the general formula I

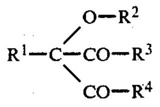
I in which $R^1$ represents optionally suibstituted alkyl, alkenyl, alkinyl, cycloalkyl, cycloalkenyl, aryl, heteroaryl, $R^2$ represents hydrogen, trialkylsilyl or optionally substituted alkyl, cycloalkyl, alkenyl, alkinyl, aralkyl, alkylcarbonyl, arylcarbonyl, alkoxycarbonyl, aryloxycarbonyl, alkylsulphenyl, arylsulphenyl, alkylsulphonyl, arylsulphonyl, alkylaminosulphonyl, dialaminosulphonyl, arylaminosulphonyl or arylalkylaminosulphonyl, or a radical of the formula $—CO—NR^5R^6$ wherein $R^5$ and $R^6$ independently of one another represent hydrogen or optionally substituted alkyl, cycloalkyl, aryl, alkylaminocarbonyl, arylaminocarbonyl, alkylcarbonyl, arylkcarbonyl, alkoxycarbonyl, aryloxycarbonyl, alkylsulphonyl or arylsulphonyl, $R^3$ and $R^4$ independently of one another represent an amino or OX radical, wherein X represents hydrogen, optionally substituted alkyl- or cycloalkyl, aralkyl or one equivalent of an alkali metal or alkaline earth metal, or $R^3$ and $R^4$ represent optionally substituted alkylamino, arylamino, aralkylamino, dialkylamino, cycloalkylamino, alkenylamino, trialkylsilylamino, trialkylsilylalkylamino or nitrogen-containing saturated heterocyclic radicals, which optionally contain further hetero-atoms, or $R^3$ and $R^4$ represent radicals of the formula $—NHR^7$ wherein $R^7$ represents hydroxyl, formyl, alkylcarbonyl, alkenylcarbonyl, cycloalkenylcarbonyl, arylcarbonyl, amino, alkylamino, arylamino, alkylarylamino, dialkylamino, alkylaminocarbonylamino

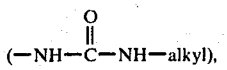

alkylaminothiocarbonylamino

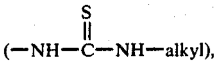

arylaminocarbonylamino, arylaminothiocarbonylamino, alkylcarbonylamino

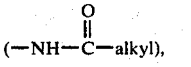

arylcarbonylamino, alkylsulphonylaminocarbonylamino

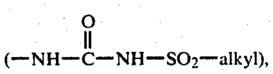

arylsulphonylaminocarbonylamino, alkylcarbonylaminocarbonylamino

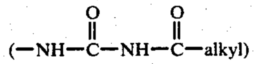

or arylcarbonylaminocarbonylamino, it being possible for the alkyl or aryl radicals to be optionally substituted, or $R^3$ and $R^4$ represent radicals of the formula

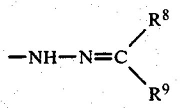

wherein $R^8$ represents optionally substituted alkyl or aryl and $R^9$ represents hydrogen or alkyl, and wherein if $R^2$ represents hydrogen, $R^3$ and $R^4$ may not at the same time represent amino, are outstandingly suitable for combating pests.

The substituted malonic acid derivatives which can be used according to the invention are particularly suitable for combating insects and arachnids. They are distinguished by a considerably better action than the compounds known for these indications from the prior art. They also have favourable values in respect of toxicity to warm-blooded animals.

The new compounds of the formula I mentioned below as preferred are preferably employed.

1. The new substituted malonic acid derivatives of the general formula I

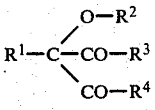
I wherein $R^1$ represents optionally substituted alkenyl, alkinyl, cycloalkyl, cycloalkenyl, aryl or heteroalkyl, $R^2$ represents hydrogen, trialkylsilyl or optionally substituted alkyl, cyloalkyl, alkenyl, alkinyl, aralkyl, alkylcarbonyl, arylcarbonyl, alkoxycarbonyl, aryloxycarbonyl, alkylsulphenyl, arylsulphenyl, alkylsulphonyl, arylsulphonyl, alkylaminosulphonyl, dialkylaminosulphonyl, arylaminosulphonyl or arylalkylaminosulphonyl, or a radical of the formula $-CO-NR^5R^6$ wherein $R^5$ and $R^6$ independently of one another represent hydrogen or optionally substituted alkyl, cycloalkyl, aryl, alkylaminocarbonyl, arylaminocarbonyl, alkylcarbonyl, arylcarbonyl, alkoxycarbonyl, aryloxycarbonyl, alkylsulphonyl or arylsulphonyl, $R^3$ and $R^4$ independently of one another represent an amino or OX radical, wherein X represents hydrogen, optionally substituted alkyl- or cycloalkyl, aralkyl or one equivalent of an alkali metal or alkaline earth metal, or $R^3$ and $R^4$ represent optionally substituted alkylamino, arylamino, aralkylamino, dialkylamino, cycloalkylamino, alkenylamino, trialkylsilamino, trialkylsilylalkylamino or nitrogen-containing saturated heterocyclic radicals, which optionally contain further hetero-atoms, or $R^3$ and $R^4$ represent radicals of the formula $-NHR^7$ wherein $R^7$ represents hydroxyl, formyl, alkylcarbonyl, alkenylcarbonyl, cycloalkenylcarbonyl, arylcarbonyl, amino, alkylamino, arylamino, alkylarylamino, dialkylamino, alkylaminocarbonylamino

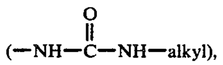

alkylaminothiocarbonylamino

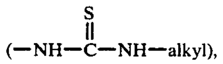

arylaminocarbonylamino, arylaminothiocarbonylamino, alkylcarbonylamino

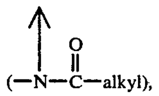

arylcarbonylamino, alkylsulphonylaminocarbonylamino

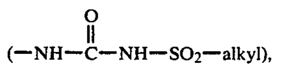

arylsulphonylaminocarbonylamino, alkylcarbonylaminocarbonylamino

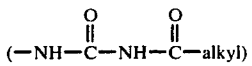

or arylcarbonylaminocarbonylamino, it being possible for the alkyl or aryl radicals to be optionally substituted, or $R^3$ and $R^4$ represent radicals of the formula

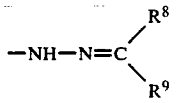

wherein $R^8$ represents optionally substituted alkyl or aryl and $R^9$ represents hydrogen or alkyl, and wherein if $R^2$ represents hydrogen, $R^3$ and/or $R^4$ may not represent amino or OX, wherein X represents alkyl or cycloalkyl, have also been found;

Preferably, in formula I, $R^1$ represents $C_{2-7}$-alkenyl, $C_{3-7}$-cycloalkyl or $C_{5-8}$-cycloalkenyl, which can be optionally substituted by one or more identical or different radicals from the following group: halogen, in particular fluorine, chlorine and bromine, $C_{1-4}$-alkoxy, in particular methoxy and ethoxy, carboxyl carbaloxy, in particular methoxycarbonyl and ethoxycarbonyl, and phenyl, phenoxy and thiophenyl, it being possible for the phenyl rings to be substituted by halogen or alkyl; or $R^1$ represents phenyl, which can optionally be substituted by one or more identical or different radicals from the following group: halogen, in particular chlorine, bromine and fluorine, nitro, amino, OH, CN, $C_{1-4}$-alkyl, in particular methyl, $C_{1-4}$-halogenoalkyl, in particular trifluoromethyl, trichloromethyl and pentafluoroethyl, $C_{1-4}$-alkoxy, methylenedioxy, ehtylenedioxy, $C_{1-4}$-halogenoalkoxy, in particular trifluoromethoxy and pentafluoroethoxy, difluoromethylenedioxy, halogen-substituted ethylenedioxy, $C_{1-4}$-alkylthio, $C_{1-4}$-halogenoalkylthio, in particular trifluoromethylthio, $C_{2-8}$-alkoxyalkyl, $C_{2-8}$-halogenoalkoxyalkyl, $C_{1-4}$-alkylsulphonyl, in particular methylsulphonyl, $C_{1-4}$-halogenoalkylsulphonyl, carboxyl and carbalkoxy, in particular methoxycarbonyl, or represents the radical $C_{1-4}$-alkoxy—N═CH—, in particular $CH_3$—O—N═CH—, or represents phenyl, phenyloxy or thiophenyl, which can optionally be substituted by halogen or $C_{1-4}$-alkyl, or represents carboxyalkoxy with 2–4 C atoms, such as carboxymethoxy, or $R^1$ represents heteroaryl, such as pyridinyl, pyrimidinyl, triazinyl, isoxazolyl, thiazolyl, oxadiazolyl, imidazolyl, triadazolyl, furanyl or thiophenyl, which can optionally be one or polysubstituted by identical or different substituents from the group comprising halogen, in particular chlorine, $C_{1-4}$-alkyl, in particular methyl and ethyl, and $C_{1-4}$-alkoxy, in particular methoxy and ethoxy.

Moreover, preferably, $R^1$ represents 3-nitrophenyl, 3-iodophenyl, biphenyl, 4-trimethylsilyloxyphenyl, 4-chloro-3-nitrophenyl, 3-chloro-4-nitrophenyl, 3,4,5-trichlorophenyl, 3,5-dichloro-4-fluorophenyl, 4-difluoromethylphenyl, 3-nitro-4-fluorophenyl, 3-fluoro-4-nitrophenyl, 3-trifluoromethyl-4-chlorophenyl, 4-trifluoromethyl-3-chlorophenyl, 3-chloro-5-trifluoromethylphenyl, 3,4-(di(trifluoromethyl)-phenyl-di(triflurormethyl)-phenyl, 3-triflurormethyl-4,5-dichlorophenyl, 4-trifluoromethyl-3,5-dichlorophenyl, 4-trifluoromethoxy-3-mitrophenyl, 4-trifluoromethoxy-3-bromophenyl, 4-nitro-3-trifluoromethoxyphenyl, 4-bromo-3-trifluoromethoxyphenyl, 3-nitro-4-trifluoromethoxy-5-chlorophenyl, 4-methoxy-3,5-dichlorophenyl, 4-methyl-3,5-dichlorophenyl, 4-fluoro-3-bromophenyl, 4-4-bromom-3-fluorophenyl, 4-chloro-3-methylphenyl, 4-trifluoromethylmercaptophenyl, 4-trifluoromethoxy-3-chlorophenyl, 3-trifluoromethyl-4-chlorophenyl, 4-chlorodifluoromethoxy-3-chlorophenyl, 4-fluoro-3-chlorophenyl, pentafluorophenyl, 4-fluoro-3,5-dibromophenyl, 4-fluoro-3-chloro-5-bromophenyl, 4-chloro-3,5-dibromophenyl, 4-bromo-3,5-dichlorophenyl, 3-bromo-4,5-dichlorophenyl, 3,4,5-trifluorophenyl or 3,4,5-trobromophenyl, 3,5-dichloro-4-aminophenyl, 3,5-dichloro-4-methoxyphenyl, 3,5-dichloro-4-hydroxyphenyl-3-chloro-4-hydroxyphenyl.

Preferably, in formula I, $R^2$ represents hydrogen, trialkylsilyl with 1–4 C atoms in the alkyl part, $C_{1-4}$-alkyl, $C_{1-4}$-alkylcarbonyl, or benzoyl, which can optionally be substituted by one or more identical or different radicals (A) as follows: (A) represents halogen, in particular chlorine, bromine or flourine, nitro, amino, CN, $C_1$-4-alkyl, in particular methyl, $C_{1-4}$-halogenoalkyl, in particular trifluoromethyl or pentafluoroethyl, $C_{1-4}$-alkoxy, $C_{1-4}$-halogenoalkoxy, in particular trifluoromethoxy or pentalfuoroethoxy, methylenedioxy, ethylenedioxy, difluoromethylenedioxy, halogen-substituted ethylenedioxy, such as trifluoroethylenedioxy, $C_{1-4}$-alkylthio, $C_{1-4}$-halogenoalkylthio, in particular trifluoromethylthio, $C_{2-8}$-alkoxyalkyl, $C_{2-8}$-halogenoalkoxyalkyl, $C_{1-5}$-alkylsulphenyl or phenylsulphenyl, which can optionally be substituted, $C_{1-4}$-alkylsulphonyl, in particular methylsulphonyl, $C_{1-4}$-halogenoalkylsulphonyl, carbaloxy, in particular methoxycarbonyl, $C_{1-4}$-alkoxy—N=CH—, in particular $CH_3$—O—N=CH—, or phenyl, phenyloxy or thiophenyl, optionally substituted by halogen or $C_{1-4}$-alkyl, or carboxyalkoxy with 2–4 C atoms, such as carboxymethoxy; or $R^2$ represents $C_{1-4}$-alkoxycarbonyl, phenoxycarbonyl, which can optionally be substituted by one or more of the radicals (A), $C_{1-4}$-alkylsulphonyl, phenylsulphonyl, which can optionally be substituted by one or more of the radicals (A), optionally substituted $C_{1-4}$-alkylaminosulphonyl, $C_{1-5}$-alkylsulphenyl or phenylsulphenyl, di-$C_{1-4}$-alkylaminosulphonyl, phenylaminosulphonyl, which can optionally be substituted by one or more of the radicals (A), phenyl-$C_{1-4}$-alkyl-aminosulphonyl or radicals of the formula

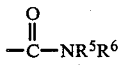

wherein $R^5$ and $R^6$ independently of one another for hydrogen, $C_{1-20}$-alkyl, $C_{3-6}$-cycloalkyl, phenyl, which can optionally be substituted by one or more of the radicals (A), phenylcarbonyl, which can optionally be substituted by one or more of the radicals (A), or $C_{1-10}$-alkylcarbonyl, $C_{1-4}$-alkylaminocarbonyl, $C_{1-10}$-alkoxycarbonyl, phenylaminocarbonyl or phenylsulphonyl, each of which can be optionally substituted by one or more of the radicals (A).

Preferably, in formula I, $R^3$ and $R^4$ independently of one another represent amino, $C_{1-8}$-amino, $C_{1-8}$-alkylamino or di-$C_{1-8}$-alkylamino, each of which can optionally be substituted by hydroxyl or $C_{1-4}$-alkoxy, phenylamino, which can optionally be substituted by one or more of the abovementioned radicals (A), $C_{5-6}$-cycloalkylamino, a saturated heterocyclic radical with 5–6 ring C atoms, such as morpholine, tri-$C_{1-4}$-alkylsilamino or radicals of the formula $—NHR^7$ $R^7$ for $C_{1-4}$-alkylcarbonyl, $C_{2-4}$-alkenylcarbonyl, $C_{5-8}$-cycloalkenylcarbonyl, such as acetyl, $C_{1-4}$-alkylamino, such as methylamino or t-butylamino, phenylamino, which can optionally be substituted by one or more of the abovementioned radicals (A), $C_{1-4}$-alkylaminocarbonylamino

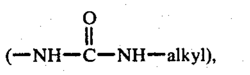

phenylaminocarbonylamino

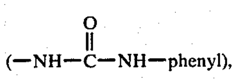

which can optionally be substituted by one or more of the radicals (A), $C_{1-4}$-alkylcarbonylamino

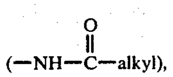

or benzoylamino, which can optionally be substituted by one or more of the radicals (A), or $R^3$ and $R^4$ represent a radical of the formula

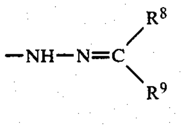

wherein $R^8$ represents $C_{1-4}$-alkyl, in particular methyl, or phenyl, which can optionally be substituted by one or more of the radicals (A), and $R^9$ represents hydrogen or $C_{1-4}$-alkyl.

Particularly preferred compounds of the formula I are those in which $R^1$ represents $C_{5-6}$-cycloalkyl, $C_{2-4}$-alkenyl, which is optionally substituted by carboxyl, or phenyl, which is optionally substituted by halogen, in particular fluorine or chlorine, $C_{1-4}$-alkyl, in particular methyl, $C_{1-4}$-alkoxy, $C_{1-4}$-halogenoalkoxy, $C_{1-4}$-halogenoalkyl, $NH_2$, $CH_3O$—N=CH—, or nitro.

Compounds of the general formula I which should be mentioned in particular are those in which $R^1$ represents phenyl, which is optionally mono-, di- or tri-substituted in the 3-, 4- and 5-positions by identical or different halogen atoms, in particular fluorine, chlorine, bromine or iodine, $R^2$ for $C_{1-4}$-alkyl, in particular methyl, optionally halogen-substituted $C_{1-4}$-alkylaminosulphonyl, $C_{1-4}$-alkylcarbonyl, in particular methylcarbonyl, optionally halogen-substituted phenylcarbonyl, phenylsulphenyl, $C_{1-4}$-alkylsulphenyl, trialkylsilyl, in particular trimethysilyl or

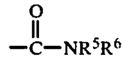

wherein $R^5$ represents hydrogen and $R^6$ represents optionally halogen-substituted phenyl or phenylcarbonyl, or $C_{1-4}$-alkyl or $C_{1-4}$-alkylcarbonyl, and $R^3$ and $R^4$ are identical or different and represent amino, trimethysilylamino, $C_{1-4}$-alkylcarboxylamino, in paricular acetylamino, or formylamino, both radicals $R^3$ and $R^4$ only representing amino if $R^2$ is other than hydrogen.

Compounds of the formula I which may be mentioned in particular are those in which $R^1$ represents phenyl, which is optionally one or polysubstituted by chlorine, $R^2$ represents trimethysilyl and $R^3$ and $R^4$ represent trimethylsilylamino.

Suprisingly, the substituted malonic acid derivatives according to the invention display a substantially more powerful insecticidal action than the carbamates which are known from the prior art and have the same type of action, such as 5,6-dimethyl-2-dimethylamino-4-pyrimidinyl dimethylcarbamate or 1-naphthyl N-methylcarbamate (U.S. Pat. Nos. 3,493,574 and 2,903,478).

The new substituted malonic acid derivatives also have a favourable toxicity and a root-systemic action.

2. It has furthermore been found that the compounds of the formula I

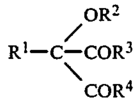

I wherein $R^1$ represents optionally substituted alkyl, alkenyl, alkinyl, cycloalkyl, cycloalkenyl, aryl, heteroaryl, $R^2$ for hydrogen, trialkylsilyl or optionally substituted alkyl, cycloalkyl, alkenyl, alkinyl, aralkyl, alkylcarbonyl, arylcarbonyl, alkoxycarbonyl, aryloxycarbonyl, alkylsulphenyl, arylsulphenyl, alkylsulphonyl, arylsulphonyl, alkylaminosulphonyl, dialkylaminosulphonyl, arylaminosulphonyl or arylalkylaminosulphonyl, or a radical of the formula $-CO-NR^5R^6$ wherein $R^5$ and $R^6$ independently of one another represents hydrogen or optionally substituted alkyl, cycloalkyl, aryl, alkylaminocarbonyl, arylaminocarbonyl, alkylcarbonyl, arylcarbonyl, alkoxycarbonyl, aryloxycarbonyl, alkylsulphonyl or arylsulphonyl, $R^3$ and $R^4$ independently of one another represent an amino of OX radical, wherein X represents hydrogen, optionally substituted alkyl- or cycloalkyl, aralkyl or one equivalent of an alkali methal or alkaline earth metal, or $R^3$ and $R^4$ represent optionally substituted alkylamino, arylamino, aralkylamino, dialkylamino, cycloalkylamino, alkenylamino, trialkylsilylamino, trialkylsilylalkylamino or nitrogen-containing saturated heterocyclic radicals, which optionally contain further hetero-atoms, or $R^3$ and $R^4$ represent radicals of the formula $-NHR^7$ wherein $R^7$ represents hydroxyl, formyl, alkylcarbonyl, alkenylcarbonyl, cycloalkenylcarbonyl, arylcarbonyl, amino, alkylanimo, arylamino, alkylarylamino, dialkylamino, alkylaminocarbonylamino

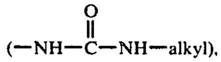

alkylaminothiocarbonylamino

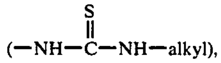

arylaminocarbonylamino, arylaminothiocarbonylamino, alkylalkylcarbonylamino

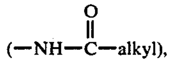

arylcarbonylamino, alkylsulphonylaminocarbonylamino

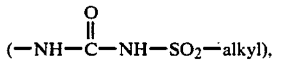

arylsulphonylaminocarbonylamino, alkylcarbonylaminocarbonylamino

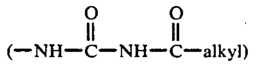

or arylcarbonylaminocarbonylamino, it being possible for the alkyl or aryl radicals to be optionally substituted, or $R^3$ and $R^4$ represent radicals of the formula

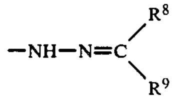

wherein $R^8$ represents optionally substituted alkyl or aryl and $R^9$ represents hydrogen or alkyl, and wherein if $R^2$ represents hydrogen, $R^3$ and $R^4$ may not at the same time represent amino or OX, wherein X represents alkyl or cycloalkyl;

are obtained by a process in which (a) if $R^3$ and $R^4$ do not represent OH, O-alkali metal or O-(alkaline earth methal)$_{\frac{1}{2}}$, compounds of the formula II

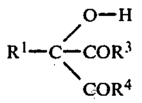

II wherein $R^1$, $R^3$ and $R^4$ have the abovementioned meaning, ($a_1$) are reacted with compounds of the formula III $R^{10}—Y$ III wherein Y represents halogen or $-O-SO_2-O-C_{1-4}$-alkyl and $R^{10}$represents optionally substituted alkyl, cycloalkyl, aralkyl, alkenyl or alkinyl, or ($a_2$) are reacted with compounds of the formula IV $R^{11}—Z$ IV wherein Z represents halogen, $C_{1-4}$-alkylcarbonyloxy or CN and $R^{11}$represents optionally substituted alkylcarbonyl, arylcarbonyl, alkoxycarbonyl, arloxycarbonyl, alkylsulphonyl, arylsulphonyl, alkylaminosulphonyl, dialkylaminosulphonyl, arylaminosulphonyl or arylalkylaminosulphonyl, or $—CONR^5R^6$ wherein $R^5$ and $R^6$ are identical or different and can represent hydrogen or optionally substituted alkyl, cycloalkyl, aryl, alkylcarbonyl, arylcarbonyl, alkylsulphonyl or arylsulphonyl, or ($a_3$) are reacted with compounds of the formula V $R^{12}—NCO$ V in which $R^{12}$ represents optionally substituted alkyl, cycloalkyl, aryl, alkylcarbonyl, arylcarbonyl, alkoxycarbonyl, aryloxycarbonyl, alkylsulphonyl or arylsulphonyl, or ($a_4$) are first reacted with compounds of the formula VI

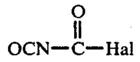

VI wherein

Hal represents halogen, and the products are then reacted with compounds of the formula VII $(R^{13})_2N—H$ (VII)

wherein the radicals $R^{13}$ independently of one another represent hydrogen, alkyl or aryl, or water, or (b) if $R^2$ represents trialkylsilyl and $R^3$ and $R^4$ do not represent OH, O-alkali metal or O-(alkaline earth metal)$_{\frac{1}{2}}$, compounds of the formula II (above are reacted with trialkylsilyl compounds of the formula VIII

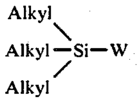

VIII in which

W represents halogen, CN or trialkylsilylamino, in approximately equimolar amounts, if appropriate in the presence of a diluent, if appropriate in the presence of a catalyst and if appropriate in the presence of an acid acceptor.

3. It has furthermore been found that the compounds of the formula IX

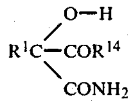

IX in which $R^1$ has the meaning given under 1 and $R^{14}$ represents amino, optionally substituted alkoxyo or cycloalkoxy, or alkylamino, arylamino, dialkylamino, cycloalkylamino, alkenylamino or nitrogen-containing saturated heterocyclic radicals which optionally contain further heteroatoms, it being possible for the radicals to be optionally substituted, are obtained by a process in which compounds of the formula X

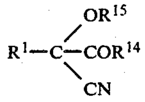

X in which $R^1$ has the meaning given under 1, $R^{15}$ represents hydrogen or $Si(CH_3)_3$ and $R^{14}$ has the abovementioned meaning, are reacted with inorganic acids.

4. It has furthermore been found that the compounds of the formula XI

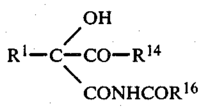

XI in which $R^1$ has the meaning given under 1, $R^{14}$ has the meaning given under 3 and $R^{16}$ represents hydrogen or optionally substituted alkyl, alkenyl, cycloalkenyl or aryl, are obtained by a process in which compounds of the formula X

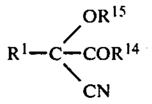

X in which $R^1$ and $R^{14}$ have the abovementioned meaning and
$R^{15}$ represents hydrogen or $Si(CH_3)_3$, are reacted with acids of the formula XII $R^{16}$—COOH XII in which $R^{16}$ has the abovementioned meaning, or their acid anhydrides, in the presence of inorganic acids.

5. It has furthermore been found that the compounds of the formula XIII

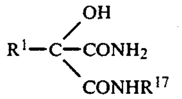

XIII in which $R^1$ has the meaning given under 1 and
$R^{17}$ represents alkyl, cycloalkyl, alkenyl, amino, alkylamino, arylamino, acylamino, dialkylamino or alkylarylamino, are obtained by a process in which compounds of the formula XIV

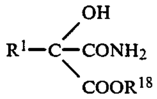

XIV in which $R^1$ has the abovementioned meaning and
$R^{18}$ represents alkyl or cycloalkyl, are reacted with compounds of the formula XV $R^{17}NH_2$ XV in which $R^{17}$ has the abovementioned meaning.

6. It has furthermore been found that the compounds of the formula XVI

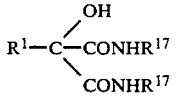

XVI in which $R^1$ and $R^{17}$ have the meaning given under 5, are obtained by a process in which compounds of the formula XVII

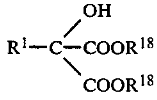

XVII in which $R^1$ has the abovementioned meaning and the radicals $R^{18}$ are identical or different and represent alkyl or cycloalkyl, are reacted with compounds of the formula XV $R^{17}NH_2$ XV in which $R^{17}$ has the abovementioned meaning.

7. It has furthermore been found that the compounds of the formula XVIII

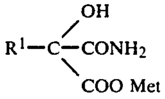

XVIII in which $R^1$ has the meaning given under 1 and
Met represents one equivalent of an alkali metal or alkaline earth metal cation, are obtained by a process in which compounds of the formula XIV

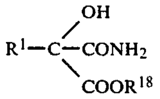

XIV in which $R^1$ and $R^{18}$ have the meaning given under 5., are reacted with compounds of the formula XIX Met—OH XIX in which Met has the abovementioned meaning.

8. It has furthermore been found that compounds of the formula XX

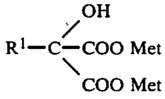

XX in which $R^1$ and Met have the meaning given under 7, are obtained by a process in which compounds of the formula XVII

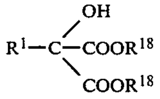

XVII in which $R^1$ and $R^{18}$ have the meanings given under 6. (above), are reacted with compounds of the formula XIX MetOH in which Met has the meaning given under 7.

9. It has furthermore been found that compounds of the formula XXI

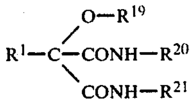

XXI in which $R^1$ has the meaning given above under 1., $R^{19}$ represents alkylcarbonyl or arylcarbonyl, $R^{20}$ represents formyl, alkylcarbonyl, alkenylcarbonyl, cycloalkenylcarbonyl or arylcarbonyl and $R^{21}$ represents hydrogen, formyl, alkylcarbonyl or arylcarbonyl, are obtained by a process in which compounds of the formula XXII

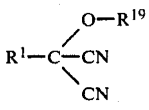

XXII in which $R^1$ and $R^{19}$ have the abovementioned meaning, are reacted with acids of the formula XXIII $R^{20}$—OH XXIII in which $R^{20}$ has the abovementioned meaning, or their anhydrides, in the presence of inorganic mineral acids, if appropriate with the addition of water.

10. It has furthermore been found that compounds of the formula XXIV

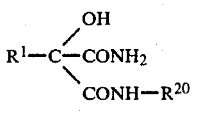

XXIV in which $R^1$ has the meaning given under 1 and $R^{20}$ represents formyl, alkylcarbonyl, alkenylcarbonyl, cycloalkenylcarbonyl or arylcarbonyl, are obtained by a process in which compounds of the formula XXV

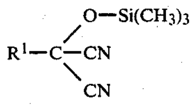

XXV in which $R^1$ has the abovementioned meaning, are reacted with acids of the formula XXIII $R^{20}$—OH XXIII in which $R^{20}$ has the abovementioned meaning, or their anhydrides, in the presence of inorganic mineral acids.

11. It has furthermore been found that compounds of the formula XXVI

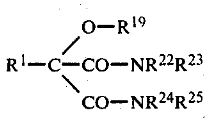

XXVI in which $R^1$ and $R^{19}$ have the meaning given under 9, $R^{22}$ represents alkylcarbonyl, $R^{24}$ represents hydrogen or alkylcarbonyl, $R^{23}$ represents hydrogen or alkyl and $R^{25}$ represents hydrogen or alkyl, are obtained by a process in which compounds of the formula XXVII

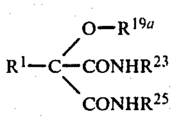

XXVII wherein $R^1$, $R^{23}$ and $R^{25}$ have the abovementioned meaning and $R^{19a}$ represents hydrogen, alkylcarbonyl or arylcarbonyl, are reacted with acid anhydrides of the general formula XXVIII

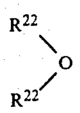

XXVIII in which $R^{22}$ has the abovementioned meaning.

12. It has furthermore been found that compounds of the formula XXIX

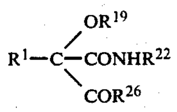

XXIX in which $R^1$, $R^{19}$ and $R^{22}$ have the meaning given under 11 and $R^{26}$ represents alkoxy or dialkylamino, are obtained by a process in which compounds of the formula XXX

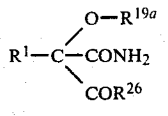

XXX in which $R^1$ and $R^{19a}$ have the meaning given under 11 and $R^{26}$ has the abovementioned meaning, are reacted witvh acid anhydrides of the general formula XXVIII

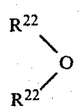

XXVIII in which $R^{22}$ has the abovementioned meaning.

13. It has furthermore been found that the compounds of the formula XXXI

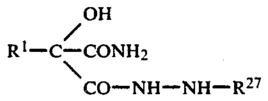

XXXI in which $R^1$ has the meaning given under 1 and $R^{27}$ represents alkylaminocarbonyl, alkylaminothiocarbonyl, arylaminocarbonyl, arylaminothiocarbonyl, alkylsulphonylaminocarbonyl, arylsulphonylaminocarbonyl, alkylcarbonylaminocarbonyl or arylcarbonylaminocarbonyl or the corresponding thiocarbonyl radicals, are obtained by a process in which compounds of the formula XXXII

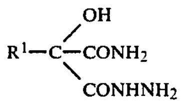

XXXII in which $R^1$ has the abovementioned meaning, are reacted with iso-(thio)-cyanates of the formula XXXIII $R^{28}NCO(S)$ XXXIII in which $R^{28}$ represents alkyl, aryl, alkylsulphonyl, arylsulphonyl, alkylcarbonyl or arylcarbonyl.

14. It has furthermore been found that the compounds of the formula XXXIV

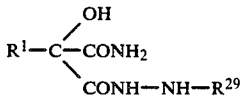

XXXIV in which in which $R^1$ has the meaning given under 1 and $R^{29}$ represents alkylcarbonyl, arylcarbonyl, alkylsulphonyl or arylsulphonyl, are obtained by a process in which compounds of the formula XXXII

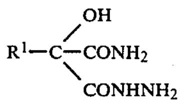

XXXII in which $R^1$ has the abovementioned meaning, are reacted with acylating agents of the formula XXXV $R^{29}$—A XXXV in which $R^{29}$ has the abovementioned meaning and A represents halogen, CN, $C_{1-4}$-alkylcarbonyloxy or arylcarbonyloxy.

15. It has furthermore been found that the compounds of the formula XXXVI

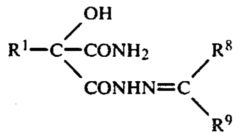

XXXVI in which $R^1$, $R^8$ and $R^9$ have the meaning given under 1, are obtained by a process in which compounds of the formula XXXII

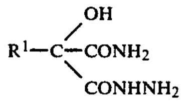

XXXII in which $R^1$ has the abovementioned meaning, are reacted with carbonyl compounds of the formula XXXVII

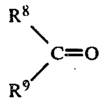

XXXVII in which $R^8$ and $R^9$ have the abovementioned meaning.

16. It has furthermore been found that the compounds of the formula XXXVIII

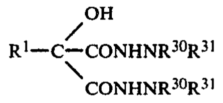

XXXVIII in which $R^1$ has the meaning given under 1, $R^{30}$ represents hydrogen and $R^{31}$ has the meanings given for $R^{28}$ and $R^{29}$ under processes 13 and 14 (above), or $R^{30}$ and $R^{31}$ together represent the radical

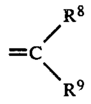

wherein $R^8$ and $R^9$ have the meaning given under 1, by a process in which the compounds of the formula XXXIX

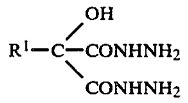

XXXIX are reacted with compounds of the formulae XXXIII, XXXV or XXXVII

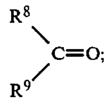

XXXVII

-continued $R^{28}NCO(S)$; XXXIII $R^{29}$—A; XXXV in which

A, $R^{28}$, $R^{29}$, $R^8$ and $R^9$ have the meanings given under 13, 14 and 15.

17. It has furthermore been found that the compounds of the formula XL

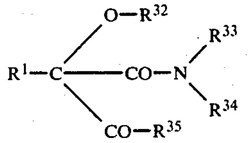

XL in which $R^1$ has the meaning given under 1, $R^{32}$ represents trialkylsilyl, alkyl, cycloalkyl, alkenyl, alkinyl, aralkyl, alkylcarbonyl or arylcarbonyl, $R^{33}$ represents hydrogen or alkyl, $R^{34}$ represents trialkylsilyl and $R^{35}$ represents alkoxy, cycloalkoxy, trialkylsilylamino, trialkylsilylalkylamino, dialkylamino or nitrogen-containing saturated heterocyclic radicals which optionally contain further hetero-atoms, it being possible for these radicals to be optionally substituted, are obtained by a process in which compounds of the formula XLI

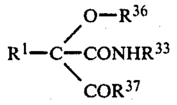

XLI in which $R^1$ and $R^{33}$ have the abovementioned meaning, $R^{36}$ represents hydrogen, alkyl, cycloalkyl, alkenyl, alkinyl, aralkyl, alkylcarbonyl or arylcarbonyl and $R^{37}$ represents alkoxy, cycloalkoxy, amino, alkylamino, dialkylamino or nitrogen-containing saturated heterocyclic radicals which optionally contain further hetero-atoms, it being possible for these radicals to be optionally substituted, are reacted with trialkylsilyl compounds of the formula VIII

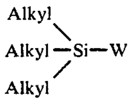

VIII in which

W has the meaning given under 2b.

18. It has furthermore been found that the compounds of the formula XLV

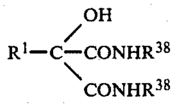

XLV in which $R^1$ has the meaning given above under 1 and $R^{38}$ represents tert.-alkyl with 4–18 C atoms, are obtained by a process in which compounds of the formula XXV

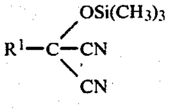

XXV in which $R^1$ has the abovementioned meaning, (a) are reacted with a tertiary alcohol of the general formula XLVI $R^{38}$—OH XLVI in which $R^{38}$ has the abovementioned meaning, in the presence of acids, or (b) are reacted with an alkene of the general formula XLVII

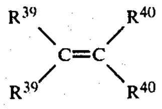

XLVII in which the radicals $R^{39}$ are identical or different and represent hydrogen or alkyl and the radicals $R^{40}$ are identical or different and represent alkyl, in the presence of acids.

19. It has furthermore been found that the compounds of the formula XLVIII

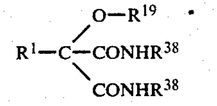

XLVIII in which $R^1$ has the meaning given under 1, $R^{38}$ has the meaning given under 18 and $R^{19}$ represents alkylcarbonyl or arylcarbonyl, are obtained by a process in which compounds of the formula XXII

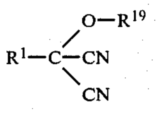

XXII in which $R^1$ and $R^{19}$ have the abovementioned meaning, (a) are reacted with a tertiary alcohol of the general formula XLVI $R^{38}$—OH XLVI in which $R^{38}$ has the abovementioned meaning, in the presence of acids, or (b) are reacted with an alkene of the formula XLVII

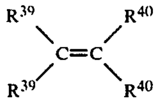

XLVII in which $R^{39}$ and $R^{40}$ have the meaning given under 18, in the presence of acids.

20. Compounds of the formula II

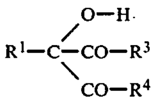

II in which $R^1$, $R^3$ and $R^4$ have the meaning given under 1, are new and are prepared by processed 3, 4, 5 , 6, 7 , 8, 13, 14, 15 and 16.

21. The compounds of the formula X

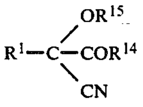

X in which $R^1$, $R^{14}$ and $R^{15}$ have the meaning given under 3 and 4, are prepared by a process in which compounds of the formula XLII

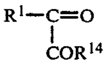

XLII in which $R^1$ and $R^{14}$ have the abovementioned meaning,

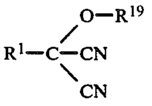

XXII are reacted with HCN or compounds which split off HCN or with trimethylsilyl cyanide.

22. The compounds of the formula X

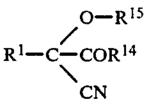

X in which.

$R^1$ has the meaning given under 1, $R^{15}$ represents hydrogen or trimethylsilyl and $R^{14}$ represents amino, alkylamino, arylamino, dialkylamino, cycloalkylamino, alkenylamino or nitrogen-containing saturated heterocyclic radicals which are bonded via nitrogen and optionally contain further hetero-atoms, it being possible for these radicals to be optionally further substituted, are new.

23. The compounds of the formula XVII

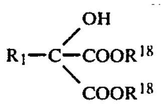

XVII in which $R^1$ and $R^{18}$ have the meaning given under 6 and 8, are obtained by a process in which compounds of the formula XXV

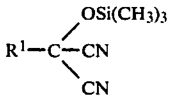

XXV in which $R^1$ has the meaning given under 1, are reacted with alcohols of the formulae XLIII $R^{18}$—OH XLIII in which $R^{18}$ has the abovementioned meaning, in the presence of inorgaic mineral acids.

24. Compounds of the formula XXII

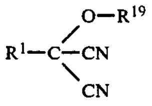

XXII in which $R^1$ and $R^{19}$ have the meaning given under 9, are known, or they can be prepared by known processes (Journ.f. prakt. Chemie, Volume [2] 39 page 260 (1889); and Chemistry a. Industry 1970 page 1408).

25. Compounds of the formula XLIV

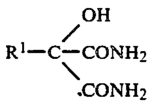

XLIV in which $R^1$ has the meaning given under 1, are prepared by a process in which compounds of the formula XXV

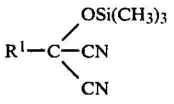

XXV in which $R^1$ has the abovementioned meaning, are hydrolysed with inorganic acids.

26. Compounds of the formula XXV

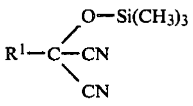

XXV in which $R^1$ has the meaning given under 1, are known, or they can be prepared by known processes (Chem. Ber. 106, page 87 (1977); Tetrahedron Letters No. 17, 1449-1450 (1973); and DE-OS (German Published Specification) No. 3,140,632).

27. Some of the compounds of the formula XLII

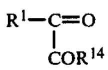

XLII in which $R^1$ and $R^{14}$ have the meaning given under 21, are known. They are prepared in a known manner (Tetrahedron Letters 1980, 3539; AnnaLen der Chemie [10], 9, 241; and DE-OS (German Published Specification) No. 2,249,820 and DE-OS (German Published Specification) No. 2,708,189).

The procedure for the processes mentioned under 2-25 (above) is described below:

Process $2a_1$

The reaction of the compounds of the formulae II and III is carried out in the presence of acid acceptors, if appropriate, in the presence of a catalyst, if appropriate, and in the presence of a diluent, if appropriate. The course of the reaction can be represented, for example, by the following equation:

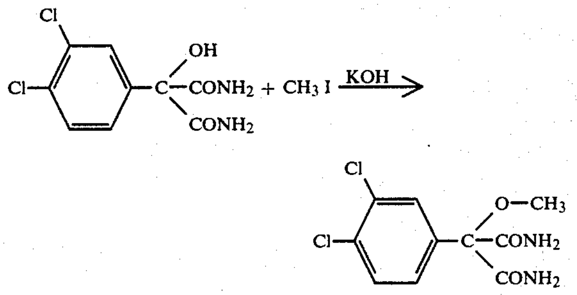

The compounds of the formulae II and III are employed in equimolar amounts, and an excess of one or other of the components provides no substantial advantages.

Compounds of the formulae II which are preferably employed are those in which the substituents $R^3$ and $R^4$ have the preferred meanings mentioned for the compounds of the formula I. Some of the compounds of the formula II are the subject of U.S. application Ser. No. 419,100, filed on Sept. 16, 1982, now pending. They can be prepared by the processes described therein. They can also be prepared by the processes descrobed below (processes 3, 5, 6, 20, 7, 10, 13, 14, 15, 16 and 24). The following compounds of the formula II may be mentioned specifically: phenyl-hydroxy-malonic acid diamide, 2-, 3-, or 4-chlorophenyl-hydroxy-malonic acid diamide, 2,3-dichlorophenyl-hydroxy-malonic acid diamide, 3,4-dichlorophenyl-hydroxy-malonic acid diamide, 3,5-dichlorophenyl-hydroxy-malonic acid diamide, 2,4-dichlorophenyl-hydroxy-malonic acid diamide, 2,5-dichlorophenyl-hydroxy-malonic acid diamide, 2,6-dichlorophenyl-hydroxy-malonic acid diamide, 2-, 3-, or 4-nitrophenyl-hydroxy-malonic acid diamide, 2-chloromethylphenyl-hydroxy-malonic acid diamide, 2-, 3-, or 4-trifluoromethylphenyl-hydroxy-malonic acid diamide, 2-, 3-, or 4-methoxyphenyl-hydroxy-malonic acid diamide, 2,6-dimethoxyphenyl-hydroxy-malonic acid diamide, 2-, 3- or 4-tolyl-hydroxy-malonic acid diamide, 2-, 3- or 4-trifluoromethoxyphenyl-hydroxy-malonic acid diamide, 2-, 3-, and 4-fluorophenylhydroxymalonic acid diamide, 3,4-dichlorophenyl-hydroxy-N-methyl-malonic acid diamide, phenylhydroxy-N,N-diethylmalonic acid diamide, the methyl ester of cyclohexylhydroxy-malonamide, 3,4-dichlorophenyl-hydroxy-malonic acid dimethyl ester, 3-chlorophenyl-hydroxy-malonic acid diethyl ester, 3,5-dichloro-4-aminophenyl-, 3,5-dichloro-4-methoxyphenyl-3,5-dichloro-4-hydroxyphenyl, 3-chloro-4-hydroxyphenyl-hydroxymalonic acid diamide of-dimethylester, the methyl ester of 3,4,5-trichlorophenyl-hydroxy-malonamide, the isopropyl ester of 4-chlorophenyl-hydroxy-malonamide, 3,5-dichlorophenyl-hydroxy-N-morpholinyl-malonic acid diamide, 3,4-dichlororphenyl-hydroxy-malonic acid bis-isopentylamide, phenylhydroxy-malonic acid bis-methylamide, cyclohexyl-hydroxy-malonic acid diamide, 2,3,4-, 2,3,6- or 3,4,5-trichlorophenylhydroxy-malonic acid diamide, 2,3,4,5-, or 2,3,5,6-tetrachlorophenyl-hydroxy-malonic acid diamide and pentachlorophenyl-hydroxy-malonic acid diamide.

Examples of the starting substances of the formula (III) which may be mentioned are methyl bromide, methyl iodide, ethyl bromide, ethyl iodide, 1-iodopropane, 2-iodopropane, allyl chloride, allyl bromide, propargyl bromide, benzyl chloride, benzyl bromide, dimethyl sulphate and diethyl sulphate.

Possible diluents are all the inert organic solvents. These include, in particular, aliphatic and aromatic, optionally halogenatd hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and p-dichlorobenzene, and furthermore ethers, such as diethyl ether and dibutyl ether, glycol dimethyl ether and diglycol dimethyl eter, tetrahydrofuran and dioxane, and also ketones, such as acetone, methyl ethyl ketone, methyl isoproplyl ketone and methyl isobutyl ketone, and in addition esters, such as methyl and ethyl acetate, and furthermore nitriles, such as, for example, acetonitrile and propionitrile, bezonitrile and glutaric acid dinitrile, and moreover amides, such as, for example, dimethylformamide, dimethylacetamide and N-methylpyrrolidone, as well as dimethylsulphoxide, tetramethylene sulphone and hexamethylphosphoric acid triamide.

All the customary acid-binding agents can be used as the acid acceptors. These include, preferably, alkali metal carbonates, hydroxides or alcoholates, such as sodium or potassium carbonate, sodium and potassium hydroxide and sodium and potassium methylate or ethylate, and furthermore aliphatic, aromatic or heterocyclic amines, for example trimethylamine, triethylamine, tributylamine, dimethylaniline, dimethylbenzylamine and pyridine.

Compounds which are customarily used for phase transfer of reactants in reactions in two-phase systems of water and water-immiscible organic solvents (phase transfer catalysts) can be used as the catalysts. Particularly preferred catalysts are tetraalkyl- and trialkylaralkyl-ammonium salts with preferably 1 to 10, in particular 1 to 8, carbon atoms per alkyl group, preferably phenyl as the aryl constituent of the aralkyl group and priferably 1 to 4, in particular 1 or 2, carbon atoms in the alkyl part of the aralkyl groups. Particularly suitable salts are the halides, such as chlorides, bromides and iodides, preferably the chlorides and bromides. Examples which may be mentioned are tetrabutylammonium bromide, benzyl-triethylammonium chloride and methyl-trioctylammonium chloride.

The reaction temperature is kept between about 0° C. and 130° C., preferably between about 20° C. and 60° C. The process is preferably carried out under normal pressure.

The end products are isolated in the generally customary manner.

Process $2a_2$

The reaction of the compounds of the formulae II and IV is carried out in the presence of acid acceptors, if appropriate, in the presence of a catalyst, if appropriate, and in the presence of a diluent, if appropriate.

The course of the reaction can be represented, for example, by the following equation:

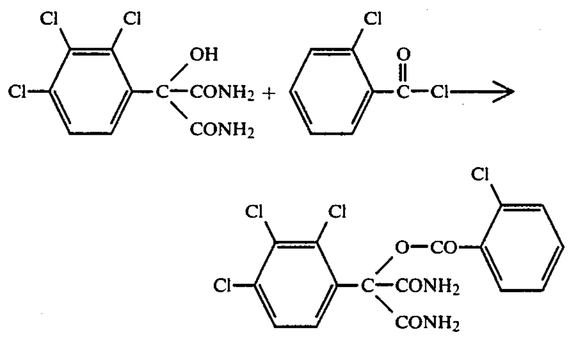

The compounds of the formula II mentioned for process $2a_1$ also be mentioned here as preferred.

Preferred compounds of the formula IV which may be mentioned are: benzoyl chloride, 3,4-dicholrobenzoyl chloride, 3-chlorobenzoyl bromide, acetyl chloride, acetic anhydride, propionyl chloride, benzoyl cyanide, ethyl chloroformate, methyl chloroformate, methylsulphamoyl chloride, dimethylcarbamoyl chloride and phenyl chloroformate.

The process can be carried out either in the presence of an acid acceptor or without a base. If it is carried out in the presence of an acid acceptor, the compounds of the formulae II and IV are employed in equimolar proportions, and a slight excess of one or other of the components provides no substantial advantages.

Possible diluents are those mentioned for process $2a_1$.

Possible acid acceptors are those mentioned for process $2a_1$. These acid acceptors in some cases also act as catalysts. Other catalysts are mentioned in the case of process $2a_1$.

Preferably, at least an equimolar amount of acid acceptor is employed, based on the compound IV. If used in excess, the acid acceptor can also serve as a diluent.

Some acid acceptors, preferably the tertiary amines, for example triethylamine or pyridine, can be added in a small amount as catalysts, and favourably influence the reaction.

The process is carried out between 0° and 130° C., preferably between 10° and 60° C. It is preferably carried out under normal pressure. The end products are isolated in the generally customary manner.

By the procedure thus far described for process $2a_2$, only a reaction of the compounds of the formula II on the hydroxyl group is achieved.

A further procedure for process $2a_2$ comprises heating the compound of the formulae II and IV in the absence of acid acceptors, if appropriate in the presence of diluents and or catalysts.

In this case, the compounds of the formula IV are employed in at least equimolar amounts, preferably in excess (1.1–10 times, preferably 1.2–5 times and in particular 1.3–3 times, the equimolar amount).

The diluents are the same as those described under $2a_1$.

The reaction is carried out between 50° and 200° C., preferably between 70° and 150° C. It is preferably carried out under normal pressure.

Possible catalysts are those mentioned for process $2a_1$. The compounds H-Z (for exsample HCl or HCN) liberated in this procedure are removed during the reaction.

By the procedure thus far described, reaction of the compounds of the formula II on the hydroxyl group is achieved.

If acid anhydrides are used as compounds of the formula IV, reaction of the compounds of the formula IV both on the hydroxyl group and, if possible, on the amide group usually takes place (compare process 11).

However, under certain conditions, the reaction with the acid anhydrides can also remain restricted to reaction of the hydroxyl group of the compounds of the formula II.

For this, it is necessary only to employ the compound II and the acid anhydride in approximately equimolar proportions.

In general terms, the reaction with acid anhydrides is carried out as described above. However, acids, such as mineral acids, for example HCl, $H_2SO_4$, $H_3PO_4$ and $HClO_4$, or strong organic acids, for example p-toluenesulphonic acid or trifluoromethanesulphonic acid, are also used as catalysts. Likewise, Lewis acids, such as, for example, $AlCl_3$, $BF_3$, ZnCl and $FeCl_3$, can also be used for this purpose.

Process $2a_3$

The reaction of the compounds of the formula II and V is carried out in the presence of a catalyst, if appropriate, and in the presence of a diluent, if appropriate.

The course of the reaction can be represented by the following equation.

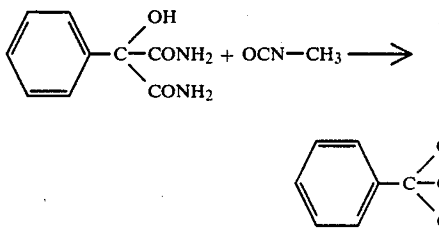

The compounds of the formula II mentioned for process $2a_1$ may also be mentioned here as preferred.

Preferred compounds of the formula B which may be mentioned are: isocyanates which are derived from the following amines: methylamine, ethylemine, propylamine, isopropylamine, butylamine, iso-butylamine, tert.-butylamine, hexylamine, dodecylamine, 2-ethylhexylamine, tetradecylamine, hexadecylamine, octadecylamine, allylamine, 2-methoxyethylamine, 2-ethoxypropylamine, 3-butoxypropylamine, 2-methylpropyl 3-aminopropanoate, 6-aminohexanenitrile, lysine esters, 1,1-aminoundecanoic acid esters, cyclohexylamine, trimethylcyclohexylamine, 2-borbornylmethylamine, aniline, o-, m- or p-chloraniline, 2,3-, 2,4-, 2,5- or 2,6-dichloroaniline, 3,4- or 3,5-dichloroaniline, p-o-nitroaniline, m-, o- or p-tolylamine, 3-trifluoromethylaniline, 3-chloro-4-methylaniline, 4-chloro-3-methylaniline, 4-chloro-3-methylaniline benzylamine, phenylcyclohexylamine and naphthylamine. Furthermore isocyanates, such as, for example, 2-ethyl-hexyl-oxy-carbonyl isocyanate, tosyl isocyanate, 3,4- or 3,5-dichloro-benzoyl isocyanate, 4-chloro-benzoyl isocyanate, 3-chloro-benzoyl isocyanate, 2,6-dichloror-benzoyl isocyanate, isopropionyl isocyanate and cyclohexylcarbonyl isocyanate.

These isocyanates are known compounds. They can be prepared by processes which are in themselves known.

Possible diluents are those mentioned for process $2a_1$.

Possible catalysts are the customary catalysts for reactions with isocyanates. Catalysts which may be mentioned are; tertiary amines, such as triethylamine, N-methylmorpholine, 1,4-diaza-bicyclo-(2.2.2)-octane (DABCO)$\beta$, $\beta'$-dimethylamino-diethyl ether and dimethylbenzylamine, and metal catalysts of Zn, Sn and Pb, such as dibutyl-tin dilaurate, dibutyl-tin oxide, tin octoate, lead octoate, zinc octoate, zinc chloride and zinc acetate.

The reaction is carried out between 50° and 150° C., preferably between 60° and 110° C. It is preferably carried out under normal pressure.

The compounds of the formulae II and V are employed in equimolar amounts, and a slight excess of one or other of the components provides no substantial advantages.

The end products are isolated in the generally customary manner.

Process $2a_4$

The reaction of the compounds of the formula II with compounds of the formula VI followed by reaction with compounds of the formula VII is carried out in the presence of diluents, if appropriate, in the presence of a catalyst, if appropriate, and in the presence of acid acceptors, if appropriate.

In the case of reaction of amines, the course of the reaction can be represented, for example, by the following equation:

(1)

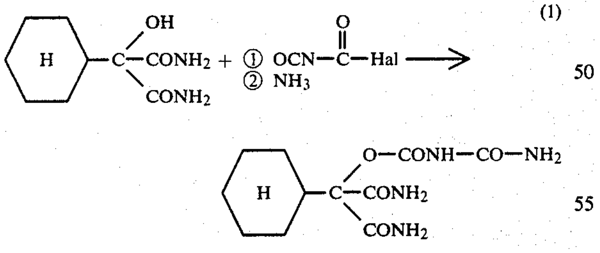

The process is carried out in two stages.

In the case of the reaction with water, the course of the reaction can be represented, for example, by the following equation:

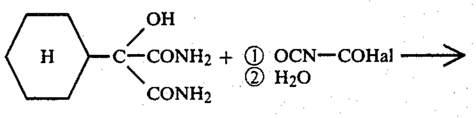

-continued

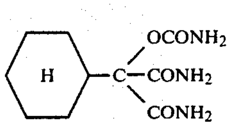

The process is carried out in two stages. Possible diluents for both process variants are those mentioned under process $2a_1$.

In general, no catalyst is required for the first stage. However, this stage can be carried out with the aid of the catalysts mentioned under $2a_1$.

The reactions are carried out at 0°–70° C., preferably at 20°–40° C.

Process 2b

If, for example, phenylhydroxymalonic acid diamide and trimethylsilyl cyanide are used as starting substances for process 2b, the reaction can be outlined by the following equation:

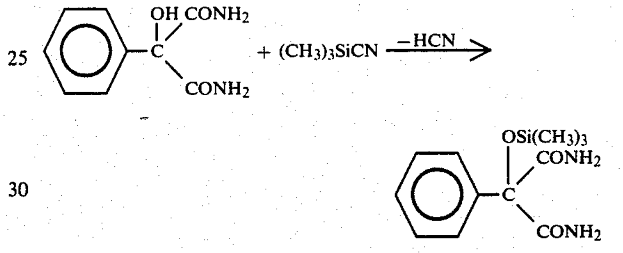

The formula II provides a definition of the hydroxymalonic acid compounds to be used as starting substances. The compounds of the formula II mentioned for process $2a_1$ may be mentioned here as preferred.

The trialkylsilyl derivatives of the formula VIII are known. Preferably, in the general formula, alkyl represents identical or different $C_{1-4}$-alkyl radicals, such as methyl and ethyl. The sugstituent W preferably represents a halogen radical, such as chlorine, or a CN radical.

Compounds which may be mentioned specifically are: trimethylsilyl chloride, trimethylsilyl bromide, trimethylsilyl iodide, trimethylsilyl cyanide and tert.-butyldimethylsilyl chloride or cyanide.

Possible diluents are those mentioned for process $2a_1$.

Possible acid acceptors and catalysts are those mentioned for process $2a_1$.

The reaction temperature is between about 0° C. and 130° C., preferably between about 20° C. and 110° C. The process is preferably carried out under normal pressure.

For carrying out process (2b) according to the invention, the compounds of the formula (II) and the trialkylsilyl compounds are usually employed in equivalent amounts.

The end products are isolated in the generally customary manner.

Process 3

If the monomethyl ester of trimethylsilyloxy-phenylmalononitrile is used as the starting substance and 96% strength sulphuric acid is used as the hydrolysing agent, the course of the reaction can be represented by the following equation:

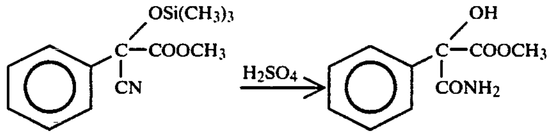

the compounds of the formula X are known in some cases, or they can be prepared analogously to known processes (Japanese Application No. 3034–729). Their preparation is described in more detail under process 21 (below).

The following compounds may be mentioned specifically:

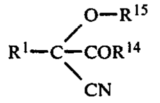

| $R^1$ | $R^{14}$ | $R^{15}$ |
|---|---|---|
| 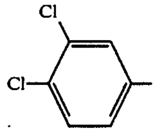 | $-OCH_3$ | H |
| 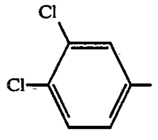 | $OC_2H_5$ | $Si(CH_3)_3$ |
| 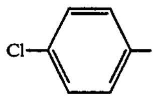 | $NH_2$ | $Si(CH_3)_3$ |
| 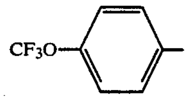 | $-N(CH_3)_2$ | H |
| 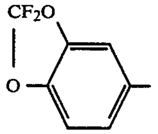 | $-N(CH_3)_2$ | $Si(CH_3)_3$ |
| 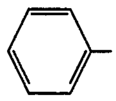 | 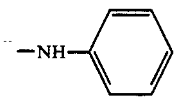 | $Si(CH_3)_3$ |
| 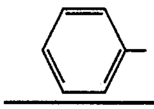 | 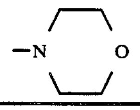 | H |

Water is generally used as the diluent for the hydrolysis. The hydrolysis can be carried out in anhydrous or water-containing acids, and only small amounts of water are frequently sufficient to obtain the desired end products.

However, the amount of water can be varied within a substantial range of from 2% to 75%, based on the amount of acid employed. It is moreover possible first to dissolve the starting substances of the formula X in an anhydrous acid and to add the required amount of water at a later point in time.

Preferred suitable acids which may be mentioned are: sulphuric acid, phosphoric acid, hydrochloric acid, hydrofluoric acid, boric acid and perchloric acid. Sulphuric acid ($H_2SO_4$) and hydrochloric acid (HCL) are particularly preferred.

In some cases, the end products of the general formula IX are somewhat water-soluble and must therefore be removed from the water with the aid of an extracting agent. Possible extracting agents are all inert organic solvents which are immiscible or only slightly miscible with water. These include toluene, xylene, chlorobenzene, dichlowobenzene, ethyl acetate, methylene chloride, chloroform, carbon tetrachloride and ether. However, an extracting agent is generally not necessary.

The reaction temperatures can be varied within a substantial range. In general, the reaction is carried out between about −15° C. and 100° C., preferably between 0° and 80° C., and in particular between 20° and 60° C.

The reaction is usually carried out under normal pressure. However, it can also be carried out under increased pressure. In general, it is carried out under pressures between about 1 bar and about 10 bar, preferably between 1 bar and 5 bar.

In carrying out the reaction, about 0.5 to 20 mols, preferably 1 to 5 mols, of inorganic acid are employed per mol of the compound of the formula X.

The compounds of the formula X dissolved in the acid is poured onto ice, after having been stirred for 30 minutes to two hours, and is isolated either by filtration with suction or by extraction. Purification is in general carried out by recrystallisation.

Process 4

The reaction of the compounds of the formula X with acids of the formula XII or their anhydrides in the presence of inorganic acids is carried out, if appropriate, in the presence of diluents.

The course of the reaction can be represented, for example, by the following equation:

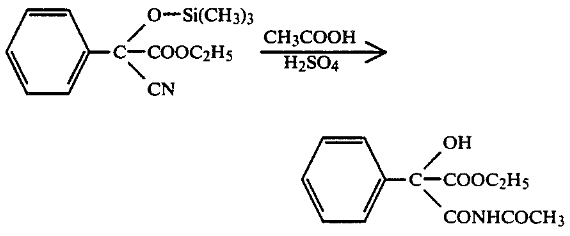

The compounds of the formula X mentioned for process 3 may also be mentioned here as preferred.

The acids mentioned for process 3 may also be mentioned here as preferred inorganic acids.

Preferred organic acids of the formula XII which may be mentioned are: formic, acetic, propionic, butyric, isobutanoic, valeric, caproic, heptylic, caprylic, capric, lauric, stearic, benzoic, phenylacetic, toluene, napthoic and mono-, di- and tri-fluoro- or -chloroacetic acid, acrylic acid, metacrylic acid and 2-cyclohexenecarboxylic acid.

The process is carried out at temperatures of 0°–100° C., preferable 20°–60° C., and preferably under normal pressure.

The process is preferably carried out without a diluent.

The reactants can be added in any desired sequence. Preferably, the compound of the formula IX is added to a mixture of the organic acid and the inorganic mineral acid.

Working up is carried out in the customary manner.

Process 5

The reaction of the compounds of the formula XIV with compounds of the formula XV is carried out, if appropriate, in the presence of a diluent.

The course of the reaction can be represented, for example, by the following equation:

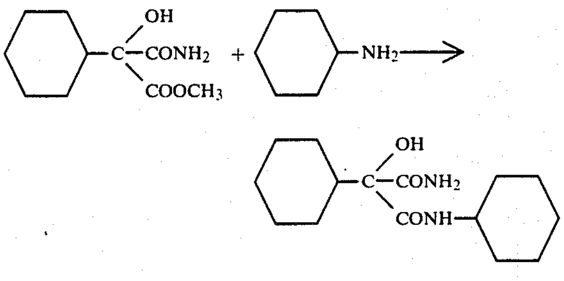

The compounds of the formula XIV are new. They are prepared by the process described under process 3 (above).

Preferred compounds which may be mentioned specifically are:

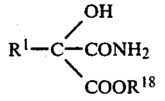

| $R^1$ | $R^{18}$ |
|---|---|
| 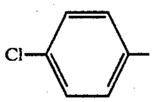 | $OCH_3$ |
| 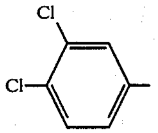 | $OC_3H_7i$ |
| 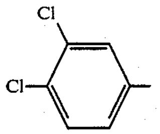 | $OC_2H_5$ |
| 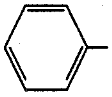 | 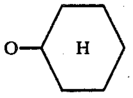 |
| 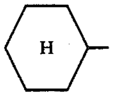 | $OC_6H_{13}$—n |

The compounds of the formula XV are known. The following preferred compounds may be mentioned: methylamine, ethylamine, propylamine, isopropylamine, butylamine, hexylamine, cyclohexylamine, neopentylamine, isopentylamine, ethanolamine, hydrazine, phenylhydrazine and acetylhydrazine.

The compounds XIV and XV are reacted in equimolar proportions. An excess of compounds of the formula XV may be advantageous.

Possible diluents are those mentioned for process $2a_1$. Additionally alcohols, such as methanol, ethanol and isopropanol, are particularly suitable solvents.

The process is carried out at 20°–120° C., preferably at 50°–100° C., and preferably under normal pressure.

Working up is carried out in the customary manner.

Process 6

The reaction of the compounds of the formula XVII with compounds of the formula XV is carried out, if appropriate, in the presence of a diluent.

The course of the reaction can be represented, for example, by the following equation:

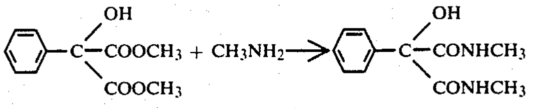

The compounds of the formula XVII are new. They are prepared by the process described under process 23 (below).

The following compounds may be mentioned as preferred: phenylhydroxymalonic acid diethyl ester, 3,4- and 3,5-dichlorophenylhydroxymalonic acid dimethyl ester and 4-chlorophenylhydroxymalonic acid diethyl ester.

The compounds of the formula XV which are preferably employed are those mentioned for process 5 (above).

The compounds of the formula XVII and XV are employed in a molar ratio of 1:2. An excess of the compound of the formula XV may be advantageous.

The reaction is carried out as described for process 5 (above).

Process 7

The reaction of the compounds of the formulas XIV with compounds of the formula XIX is carried out in the presence of diluents.

The course of the reaction can be represented, for example, by the following equation:

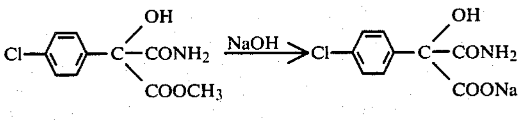

The compounds of the formula XIV are new. They are prepared by the process described under process 3 (above). The compounds mentioned for process 5 (above) are preferred.

Preferred compounds of the formula XIX which may be mentioned are alkali metal or alkaline earth metal hydroxides, such as NaOH, KOH and $Ca(OH)_2$.

The compounds XIV and XIX are employed in stoichiometric proportions.

The process is carried out from 10° to 80° C., preferably at 20°–40° C.

Preferred possible diluents are water and alcohols, such as methanol, ethanol and isopropanol and mixtures thereof with one another and with water. The process can also be carried out in a two-phase system of water and a water-immiscible organic diluent. In this case, it is preferably carried out in the presence of the abovementioned phase transfer catalysts.

Working up is carried out by customary removal of the diluent.

Process 8

The reaction of the compounds of the formula XVII with compounds of the formula XIX is carried out in the presence of diluents.

The course of the reaction can be represented, for example, by the following equation:

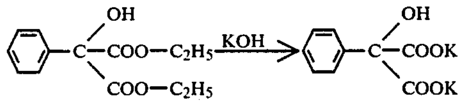

The compounds of the formula XVII are new. They are prepared by the process described under process 23 (below).

The compounds mentioned for process 6 (above) may be mentioned specifically as preferred.

The process is carried out as described for process 7 (above).

Process 9

The reaction of the compounds of the formula XXII with acids of the formula XXIII or their anhydrides is carried out, if appropriate, in the presence of diluents.

The course of the reaction can be represented, for example, by the following equation:

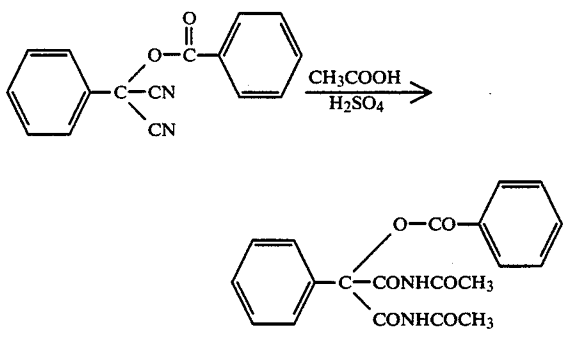

Some of the compounds of the formula XXII are known. They can be prepared by known processes. (Journ. f. prakt. Chemie [2] 39, page 260 (1889); and Chemistry a. Industry 1970 page 1408).

Compounds which may be mentioned specifically are:

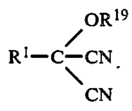

| $R^1$ | $R^{19}$ |
|---|---|
| 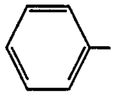 | 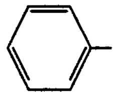 |

-continued

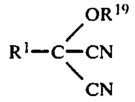

| $R^1$ | $R^{19}$ |
|---|---|
| 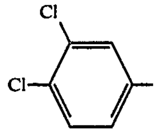 | 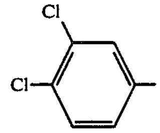 |
| 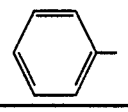 | $(CH_3)_3C-$ |

The acids mentioned for process 3 may be mentioned as preferred inorganic mineral acids.

The acids mentioned under process 4 (above) may be mentioned as preferred organic acids of the formula XXIII.

The process is carried out as described for process 4 (above).

Process 10

The reaction of the compounds of the formula XXV with acids of the formula XXIII or their anhydrides is carried out, if appropriate, in the presence of diluents.

The course of the reaction can be represented, for example, by the following equation:

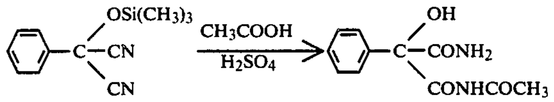

Some of the compounds of the formula XXV are known. They can also be prepared by processes which are in themselves known (Chem. Berichte 106, 587 (1973); and Tetrahedron Letters No. 17, 1449–1450 (1973)). Preferred compounds which may be mentioned are: o-, m- or p-chlorophenyl-, 2,3-dichlorophenyl-, 3,4-dichlorophenyl-, 2,4-dichlorophenyl-, 2,5-dichlorophenyl, 2,6-dichlorophenyl-, o-, m- or p-nitrophenyl-, o-chloromethylphenyl-, o-, m- or p-methoxyphenyl-, 2,6-dimethoxyphenyl-, o-, m- or p-tolyl-, o-, m- or p-trifluoromethoxyphenyl-, o-, m- or p-fluorophenyl-, and cyclohexyl-trimethylsilyloxymalonic acid nitrile.

The acids mentioned for process 3 may be mentioned as preferred inorganic mineral acids.

The acids mentioned under process 4 (above) may be mentioned as preferred organic acids of the. formula XXIII.

The process is carried out as described for process 4 (above).

Process 11

The reaction of the compouns of the formula XXVII with acid anhydrides of the formula XXVIII is carried out in the presence of diluents, if appropriate, and in the presence of catalysts, if appropriate.

The course of the reaction can be represented, for example, by the following equation:

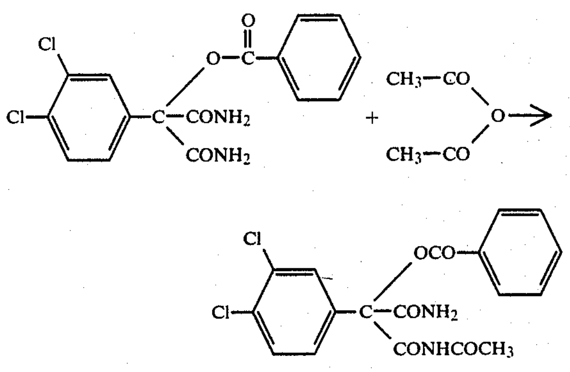

The compounds of the formula XXVII are new. Some of them are the subject of an earlier Application which has been filed by the Applicant Company and does not yet belong to the prior art (German Application No. P 31 40 275.5).

They can be obtained by the processes described under $2a_2$ and $2a_1$.

The compounds listed under $2a_2$ may be mentioned as preferred. The O-benzoyl, O-acetyl, O-3,4-dichlorobenzoyl, O-4-chlorobenzoyl, O-3-chlorobenzoyl and O-propionyl derivatives of the hydroxymalonic acid amides listed under $2a_2$ and the N-methyl-hydroxymalonamides and hydroxymalonic acid bis-methylamides corresponding to these may additionally be mentioned.

Acid anhydrides of the formula XXVIII are known. Acetic anhydride and propionic anhydride may be mentioned as preferred.

The reaction is carried out by reacting at least the stoichiometric amount of anhydride with the compound XXVII. Reaction of the hydroxyl group and, in addition, reaction at one or both amide groups, depending on the amount of anhydride added and the reaction time, thereby take place.

Possible diluents are those mentioned for process $2a_2$.

Preferably, the process is carried out in the presence of, as the diluent, the anhydride employed.

Possible catalysts are mineral acids, such as HCl, $H_2SO_4$, $H_3PO_4$ and $HClO_4$. The catalyst is added in an amount of 0.01–10% of the reaction mixture.

The process is carried out at 20°–120° C., preferably 40°–90° C.

Working up is carried out in the customary manner.

Process 12

The process conditions for process 12 are identical to those for process 11. The starting compounds of the formula XXX are new. They are obtained by the processes described under $2a_2$ and $2a_1$. The starting compounds mentioned as preferred for process $2a_1$ may also be mentioned as preferred here.

Process 13

The reaction of the compounds of the formula XXXII with the isocynanates of the formula XXXIII is carried out in the presence of diluents, if appropriate, and in the presence of catalysts, if appropriate.

The course of the reaction can be represented, for example, by the following equation:

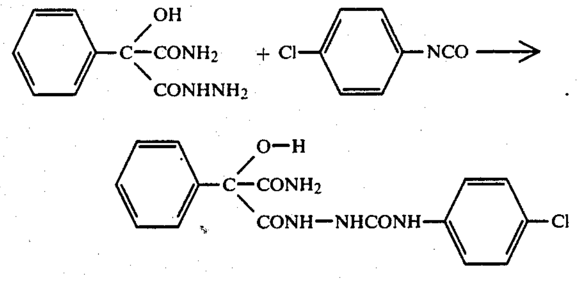

The compounds of the formula XXXII are new. They are prepaed by the processes described under 5. The compounds of the formula XXXII prepared from the starting compounds mentioned as preferred under 5 are preferred.

Isocyanates of the formula XXXIII are known. Those mentioned for process $2a_3$ are preferably used.

The diluents and catalysts mentioned for process $2a_3$ are used.

In general, the compounds XXXII are initally introduced into the diluent and are reacted with the isocyanates at temperatures of 0°–100° C., preferably 10°–50° C.

Working up is carried out in the customary manner.

Process 14

The reaction of the compounds of the formula XXXII with the acylating agents of the formula XXXV is carried out in the presence of diluents, if appropriate, in the presence of catalysts, if appropriate, and in the presence of acid acceptors, if appropriate.

The course of the reaction can be represented, for example, by the following equation:

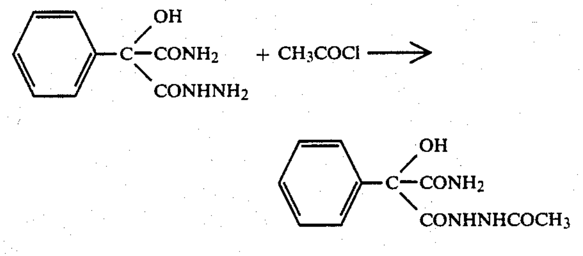

Compounds of the formula XXXII are new. They are prepared by the process described under 5. The compounds of the formula XXXII prepaed from the starting compounds mentioned as preferred under 5 are preferred.

Compounds of the formula XXXV are known. Compounds in which $R^{29}$ represents $C_{1-4}$-alkylcarbonyl, optionally substituted phenylcarbonyl, $C_{1-4}$-alkylsulphonyl or phenylsulphonyl are preferably employed.

Compounds which may be mentioned in particular are: benzoyl chloride, 3,4-dichlorobenzoyl chloride, 3-chlorobenzoyl bromide, acetyl chloride, acetic anhydride, propionyl chloride, methanesulphonyl chloride, benzoyl cyanide and tosyl chloride.

Possible diluents are those mentioned for process $2a_1$.

Possible acid acceptors are those mentioned for process $2a_1$.

The compounds of the formulae XXXII and XXXV are preferably reacted in the stoichiometric ratio (1:1). A slight excess of one or other of the components provides no substantial advantages.

The acid acceptor is preferably employed in at least the equimolar amount, based on the compound XXXV. If employed in excess, it can also serve as the diluent. Some acid acceptors, in particular the tertiary amines, such as triethylamine and pyridine, can be employed in a small amount as catalysts, and favourably influence the reaction.

The process is carried out from 0° to 100° C., preferably 10° to 60° C.

Working up is carried out in the customary manner.

Process 15

The reaction of the compounds of the formula XXXII with the carbonyl compounds of the formula XXXVII is carried out, if appropriate, in the presence of a diluent.

The course of the reaction can be represented, for example, by the following equation:

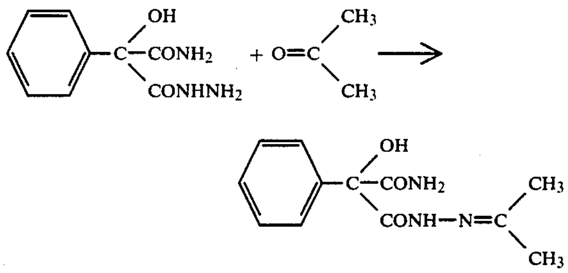

The statements made in relation to process 14 apply to the compounds of the formula XXXII.

The compounds of the formula XXXVII are known.

Compounds of the formula XXXVII in which $R^8$ and $R^9$ have the abovementioned preferred meanings are preferably employed.

Specific compounds which may be mentioned are: acetaldehyde, chloral, benzaldehyde, p-chlorobenzaldehyde, acetophenone, acetone and methyl ethyl ketone.

Possible diluents are those mentioned for process 5.

The process is carried out at 20°-120° C., preferably 50°-100° C.

The compounds of the formula XXXII and XXXVII are employed in approximately equimolar proportions. The carbonyl compounds of the formula XXXVII can be employed in excess, and in some cases as the diluent.

Working up is carried out in the customary manner.

Acids, such as p-toluenesulphonic acid, HCl and $H_2SO_4$, or bases, such as triethylamine, pyridine and NaOH, can additionally be added as catalysts to accelerate the reaction.

Process 16

The reaction of the compounds of the formula XXXIX with the compounds of the formulae XXXIII, XXV or XXXVII is carried out as described for processes 13, 14 and 15.

The compounds of the formula XXXIX are new. They are prepared as described for process 6.

The compounds of the formula XXXIX which are prepared from the starting compounds mentioned as preferred for process 6 are preferably employed.

The compounds XXXIX and XXXIII, XXXV or XXXVII are in each case reacted in the stoichiometric ratio (1:2). A slight excess of one or other of the components provides no substantial advantage.

Process 17

The reaction of the compounds of the formula XLI with trialkylsilyl compounds of the formula VIII is carried out in the presence of diluents, if appropriate, and in the presence of catalysts, if appropriate.

The course of the reaction can be represented, for example, by the following equation:

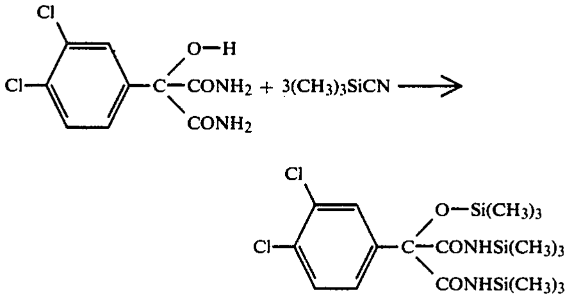

The trialkylsilyl compounds are known. Those mentioned for process 2b are preferred.

The compounds of the formula XLI are mentioned as starting materials of the formula II in process $2a_2$. The compounds of the formula LI mentioned as preferred for process $2a_2$ are alos preferred here. Further compounds of the formula XLI are those reaction products of the compounds of the formula II according to process 2 containing at least one amide hydrogen.

Those compounds of the formula XLI which result from reacting the preferred educts of proces $2a_2$ are preferred.

Possible diluents are those mentioned in process 2b. If appropriate, the reaction can also be carried out without a diluent.

The starting materials will be at least equimolar, that is to say at least 1 equivalent of trialkylsilyl compound per amide to be silylated and, if appropriate, hydroxyl group.

Preferably, an excess of the trialkylsilyl compound is employed.

Possible catalysts are the catalysts and/or acid acceptors mentioned for process 2b.

Working up is carried out in the custamary manner.

Process 18

The reaction of the comounds of the formula XXV and XLVI or XLVII is carried out in the presence of acids, and if appropriate in the presence of diluents. The course of the reaction can be represented by the following equations:

(a)

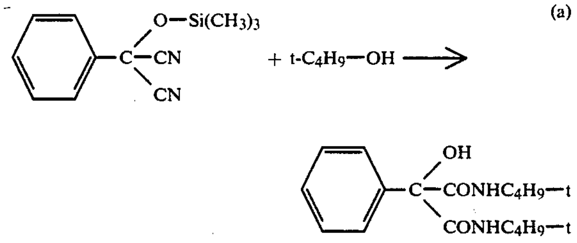

(b)

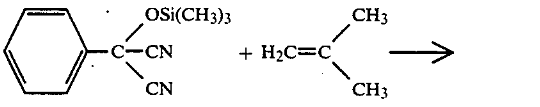

-continued

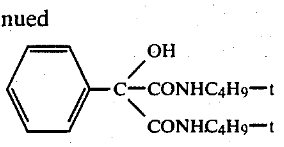

The compounds of the formula XXV mentioned for process 10 are preferably employed.

Preferred alcohols of the formula XLVI which may be mentioned are t-butanol and 2-methyl-butan-2-ol.

Preferred olefins of the formula XLVII which may be mentioned are isobutene, 2-methylpent-1-ene, 2,4,4-trimethylpent-2-ene, 2-methylbut-2-ene and 2-methylbut-1-ene.

The reaction of the compounds of the general formula XXV with the tertiary alcohols of the general formula XLVI or the alkenes of the general formula XLVII is carried out under the conditions of the so-called "Ritter reaction" or "Graf-Ritter reaction" (JACS 70, 4045 (1948); JACS 70, 4048 (1948); and Methodicum Chimicum, Volume 6 (1974). It is surprising that the quite unstable compounds of the formula XXV are available for this reaction, since splitting off of hydrocyanic acid by treatment with acid was much rather to be expected.

The reaction can be carried out in the absence of a solvent, but is advantaeously carried out in the presence of an organic solvent, and in particular acids, such as acetic acid, or optionally halogenated hydrocarbons, such as methylene chloride, can be used. Other solvents which can be used are ethers, such as dibutyl ether and diisopropyl ether, and anhydrides, such as acetic anhydride.

The reaction temperature can be varied within wide limits. Temperature between $-20°$ and $+50°$ C. are preferred.

The reactants are advantageously employed in amounts such that more than the stoichiometric amounts of alcohol or alkene are present per mol of the compounds of the formula XXV. For example, it is possible to use 2 to 40 mols, preferably 3–4 mols, of the alcohol or alkene per mol of compound of the formula XXV.

The acid is also advantageously used in a slight excess. For example, 2 to 20 mols, preferably 2.2 to 3 mols, of acid can be used per mol of compound of the formula XXV.

Sulphuric acid is preferably used as the acid, but other sulphonic acids, such as benzenesulphonic acid, may also be employed.

After hydrolysis of the reaction mixture, the compounds of the formula XLV can be isolated in a manner which is in itself known, for example by crystallisation or extraction with subsequent crystallisation or distillation.

In some cases, for example if $R^1$ denotes a lower alkyl radical, process variant b) (reaction with alkenes) may be preferable to variant a) (reaction with an alcohol).

Process 19

The reaction of the compounds of the formula XXII with alcohols or alkenes of the formulae XLVI and XLII is carried out under conditions analogous to those described for process 18.

Process 21

The reaction of the compounds of the formula XLII with HCN, compounds which split off HCN or trimethylsilyl cyanide is carried out in the presence of diluents, if appropriate, and in the presence of catalysts, if appropriate.

The course of the reaction can be represented, for example, by the following equation:

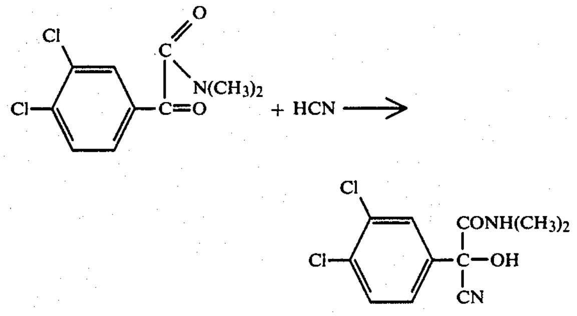

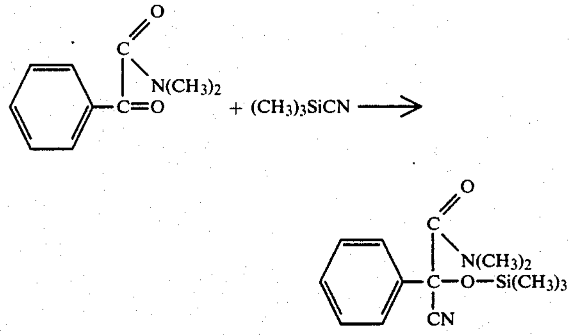

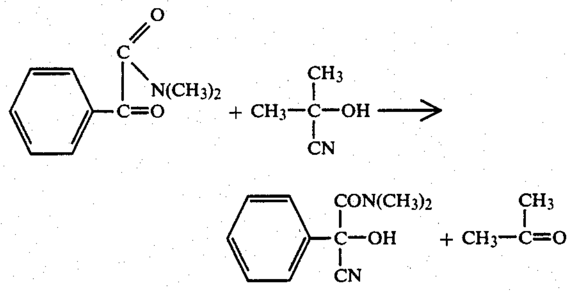

Substances which split off HCN and which can be used here are cyanohydrins, and acetone cyanohydrin or benzaldehyde cyanohydrin may be mentioned as examples.

The conversion of compounds of the formula XLII into compounds of the formula X proceeds by methods which are known in the literature, in the presence of small amounts of alkaline catalysts, for example sodium cyanide, potassium cyanide or tertiary amines, such as triethylamine, as well as alkali metal and alkaline earth metal hydroxides and carbonates.

Whilst the addition reaction of molar amounts of HCN or trimethylsilyl cyanide proceeds slightly exothermically even at room temperature and has ended when addition of the reagents is complete, the mixture must be heated for some time if cyanohydrins are used, in order to achieve complete conversion. In this case, it is also appropriate to add more than 1 mol of cyanohydrin per mol of α-keto compound of the formula XLII. Preferably, 1.1–3, preferably 1.2–2, mols of cyanohydrin are used. The excess is distilled off again when the reaction has ended.

The reactions in general proceed in the absence of a diluent, but in some cases it may be entirely appropriate to use solvents which are inert towards the products and educts, such as, for example, methanol, ethanol, isopropanol, toluene, chlorobenzene, methylene chloride, carbon tetrachloride, acetonitrile, glutaric acid dinitrile, dioxane and diethyl ether.

The reaction conditions for the reactions are very variable. Thus, for example, more than the stoichiometric amounts of HCN and trimethylsilyl cyanide can also be employed, but more than a 10% molar excess no longer provides any advantages at all. Likewise, the reaction temperature can be varied within wide limits; the reaction can be carried out in the temperature range from −50° to 300° C., and at higher temperatures the reactions are carried out either in the gas phase or in the liquid phase under pressure. However, in this case also, there is no significant advantage in comparison with the preferred experimental parameters first described.

Process 23

The process is described in an earlier application which has been filed by the Applicant Company and does not yet belong to the prior art (German Application No. P 31 40 275.5).

The process for the preparation of the compounds of the formula XVII can be carried out by the following methods of Pinner (A. Pinner, die Imidoether und ihre Derivative (The imido-ethers and their derivatives), Berlin 1882).

In these methods, in general, the compound containing nitrile groups is reacted either with hydrochloric acid or with sulphuric acid in alcoholic solution and water.

Both methods are described by way of example in the following text, but without thereby restricting the general applicability of the processes.

Hydrolysis with sulphuric acid:

100–1,000 g of sulphuric acid (100%), 2–25 mols of the alcohol of the formula $R^2OH$ and 1 mol of water are employed per mol of the compound of the formula XXV. Marked deviation from the stoichiometry in metering in the amount of water leads to losses in yield. Any water content in the starting substances (alcohol and sulphuric acid) can be taken into consideration in the amount of water to be added. The reaction solution is stirred at temperatures of 0°–150° C., preferably 20°–100° C. and particularly preferably 60° –90° C., for 1–20 hours. If appropriate, the reaction can be carried out under increased pressure. Ice-water is then stirred in, the mixture is extracted cold with a customary organic solvent, such as, for example, methylene chloride, toluene or ethyl acetate, and, if appropriate, the product is purified by distillation.

However, the process variant in which the alcohol, acid and water are taken and the compounds of the formula XXV are then added is particularly preferred here.

The reaction procedure for inverse Pinner esterification with hydrochloric acid is described below by way of example:

A 2–20-fold molar excess - based on the compound of the formula XXV—of the absolute alcohol is taken and is saturated with HCl gas at −10° to +10° C. At least 2 mols of HCl must be taken up for 1 mol of compound of the formula XXV. The reaction component of the formula XXV is added dropwise at −20° to +10° C., preferably at −10° C., and the mixture is then subsequently stirred at a maximum temperature of 30° C. for about 1 hour, before the stoichiometric amount of water, based on the CN groups employed, is added, if appropriate diluted in alcohol.

Too high or too low an amount of water leads to losses in yield.

After the mixture has been subsequently stirred for about a further hour at 0°–50° C., it is worked up.

Distillation of the compounds of the formula XVII should be disregarded if their boiling points significantly exceed 160° C. under the distillation conditions.

Process 25

The hydroxy-malonic acid diamides of the formula XLIV are the subject of an application which has been filed by the Applicant Company and does not yet belong to the prior art. They are obtained, for example, by hydrolysis of trimethylsilyloxymalonic acid dinitriles with inorganic acids, such as sulphuric acid, phosphoric acid, hydrochloric acid, hydrofluoric acid and boric acid, preferably sulphuric acid and hydrochloric acid, at temperatures between −15° C. and 100° C., preferably between 0° C. and 80° C., if appropriate using water as a diluent (German Application No. P 31 40 275.5).

The trimethylsilyloxymalonic acid nitriles to be used as intermediates for the preparation of the new compounds of the formula XXV are known (Chem. Ber. 106, (1973), or Tetrahedron Letters 17, 1449–1450 (1973), or they can easily be prepared by the methods described in these references.

Examples which may be mentioned of the starting substances of the formula (II) are: phenyl-hydroxy-malonic acid diamide, 2-, 3- or 4-chlorophenyl-hydroxy-malonic acid diamide, 2,3-dichlorophenyl-hydroxy-malonic acid diamide, 3,4-dichlorophenyl-hydroxy-malonic acid diamide, 3,5-dichlorophenyl-hydroxy-malonic acid diamide, 2,4-dichlorophenyl-hydroxy-malonic acid diamide, 2,5-dichlorophenyl-hydroxy-malonic acid diamide, 2,6-dichlorophenyl-hydroxy-malonic acid diamide, 2-, 3- or 4-nitrophenyl-hydroxy-malonic acid diamide, 2-chloromethylmethyl-phenyl-hydroxy-malonic acid diamide, 2-, 3- or 4-trifluoromethylphenyl-hydroxy-malonic acid diamide, 2-, 3- or 4-methoxyphenyl-hydroxy-malonic acid diamide, 2,6-dimethoxyphenyl-hydroxy-malonic acid diamide, 2-, 3- or 4-tolyl-hydroxy-malonic acid diamide, 2-, 3- or 4-trifluoromethoxyphenyl-hydroxy-malonic acid diamide and 2-, 3- or 4-fluorophenyl-hydroxymalonic acid diamide.

The active compounds are well tolerated by plants, have a favourable level of toxicity to warm-blooded animals, and are suitable for combating animal pests, especially insects and arachnids, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermpatera, for example, *Forficula auricularia.* From the order of the Isoptera, for example, Reticulitermes Spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and Thrips tabaci. From the order of the Heteroptera, for example, Eurygaster spp., *Dysdercus intermediu, Peisma quadrata, Cimex lecturlarius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis Fabae, Doralis pomi, Erisoma Lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Psuedococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia Litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia pondana, Capua reticulana, Choristoneura fumiferana, Clysia ambiguella, Homona magnanima* and *Tortrix viridana. From the order of the Coleoptera, for example, Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenue spp. Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca supp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnids, for example, *Scorpio maurus* and Latrodectus mactans. From the order of the Acarina, for example, *Acarus siro,* Argas spp., *Ornithodoros spp., Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foram-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example Ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially avaialbe formulations and in the use forms, prepared from these formulations, as a mixture with other active compounds, such as insecticides, baits, sterilising agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites, preferably ectoparasitic insects, in the field of livestock husbandry and animal breeding.

The active compounds according to the invention are used here in a known manner, such as by oral administration or by dermal application, for example in the form of dipping, spraying, pouring on and spotting on, and dusting.

PREPARATION EXAMPLES

Example 1

Process $2A_1$

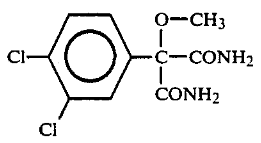

Process $2a_1$ 30 g (0.114 mol) of 3,4-dichloro-phenyl-hydroxymalonic acid diamide are initially introduced into 60 ml of dimethylsulphoxide. 6.38 g (0.144 mol) of potassium hydroxide in 150 ml of water, followed by 16.1 g (0.114 mol) of methyl iodide are then added dropwise. The reaction is exothermic: the temperature rises to about 50° C. The mixture is allowed to cool and is subsequently stirred at 20° C. for 16 hours. The solid which has precipitated is filtered off with suction and washed with water and then with petroleum ether.

Recrystallisation from ethyl acetate gives 14.1 g (44.3% of theory) of 2-(3,4-dichlorophenyl)-2-methoxymalonic acid diamide of melting point 211° to 213° C.

Example 2

Process $2a_2$

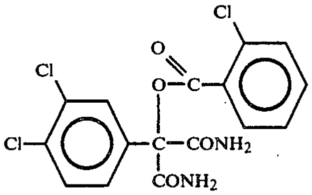

26.3 g of 3,4-dichlorophenylhydroxymalonic acid diamide were dissolved in 50 ml of pyridine, and 17.1 g of o-chlorobenzoyl chloride were added at below 30° C. After one hour, the mixture was stirred into cold 1NCl, the precipitate was taken up in ethyl acetate, the mixture was extracted by shaking and the extract was worked up. 26.5 g of crude product remained, and were recrystallised from 400 ml of ethanol. 13 g of pure 3,4-dichlorophenyl-(2-chlorobenzoyloxy)-malonic acid diamide of melting point 220° C. were obtained.

Example 2a 3,4-Dichlorophenyl-(3,4-dichlorobenzoyloxy)malonic acid diamide of melting point 237° C. (decomposition) was obtained analogously to the above process.

Example 3

Process $2a_2$

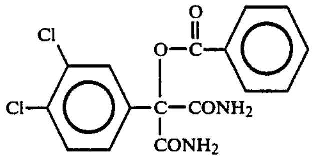

13.1 g of 3,4-dichlorophenylhydroxymalonic acid diamide in 200 ml of benzoyl chloride were heated to 110° C. for 9 hours. The mixture was then cooled to 5° C. and the precipitate was filtered off with suction, washed with toluene and then recrystallised from 550 ml of i-propanol. 10 g of 3,4-dichlorophenylbenzoyloxymalonic acid diamide were isolated: melting point 225° C., with decomposition.

Example 4

Process $2a_2$

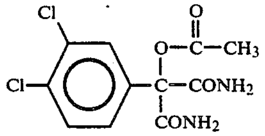

131 g of 3,4-dichlorophenylhydroxymalonic acid diamide, 850 ml of tetrahydrofuran and 750 ml of acetyl chloride were heated under reflux for 4 hours. After cooling, the precipitate was filtered off with suction and washed with i-propanol. 115 g of 3,4-dichlorophenylacetoxymalonic acid diamide of melting point 206° C. were obtained.

EXAMPLE 5

Process 2a2

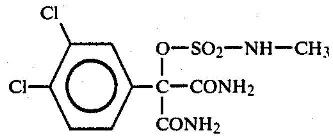

26.3 g of 3,4-dichlorophenylhydroxymalonic acid diamide were dissolved in 70 ml of pyridine, and 18 g of methylsulphamoyl chloride were added at room temperature.

After 3 hours, the mixture was stirred into cold 1N HCl and extracted with ethyl acetate and the organic phase was worked up. 17 g of 3,4-dichlorophenylmethylsulphamoyloxymalonic acid diamide of melting point 124° C. were isolated.

Example 6

Process 2a3

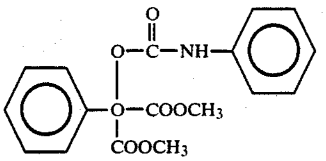

22.4 g of phenylhydroxymalonic acid dimethyl ester were dissolved in 100 ml of ethyl acetate and the solution was heated under reflux with 11.9 g of phenyl isocyanate and 2 drops of dibutyl-tin dilaurate for 3 hours. After cooling, the mixture was filtered with suction and the residue was recrystallised from toluene. 11 g of phenyl-(phenylaminocarbonyloxy)-malonic acid dimethyl ester remained; melting point 170° C. (with severe decomposition).

Example 7

Process 2a3

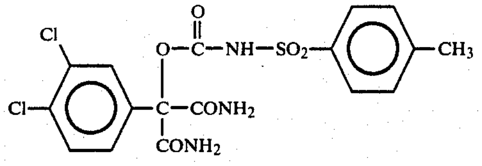

26.3 g of 3,4-dichlorophenylhydroxymalonic acid diamide were dissolved in 350 ml of ethyl acetate at 65° C., and a solution of 19.7 g of p-toluenesulphonyl isocyanate was slowly added. After the mixture had been kept at 70° C. for 1 hour, it was cooled and filtered off with suction. 14 g of 3,4-dichlorophenyl-p-toluenesulphonylaminocarbonyloxy-malonic acid diamide (melting point 178° C., decomposition) were obtained. Further product was to be isolated from the mother liquor.

Example 8

Process 2a3

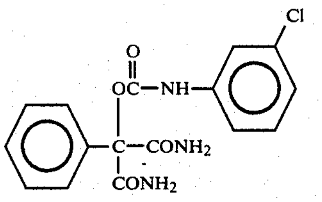

0.5 g of zinc octoate and 4.45 g of 3-chlorophenyl isocyanate were added to 8.2 g of phenylhydroxymalonic acid diamide in 30 ml of ethyl acetate and the mixture was kept at 50° C. for 30 minutes. After cooling, the precipitate was filtered off with suction and recrystallised from acetone. 5.6 g of phenyl-(3-chlorophenylaminocarbonyloxy)-malonic acid diamide of melting point 196°-198° C. were obtained.

The following isocyanate-reaction products were obtained according to the above instructions:

| | | |
|---|---|---|
| (9) | 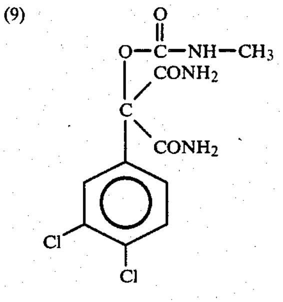 | Melting point: 199° C.<br>Acetonitrile |

-continued
(10)
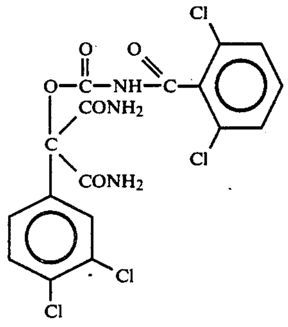
Melting point: 189-191° C.
(11)
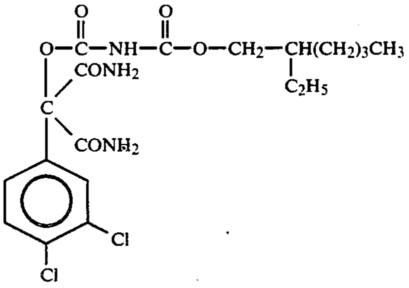
Melting point = 184–185° C.
(12)
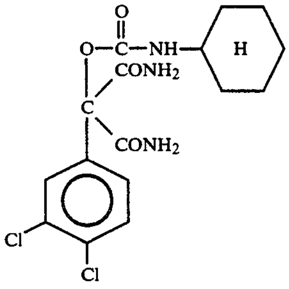
Melting point = 197–99° C.
(n-Butanol)
(13)
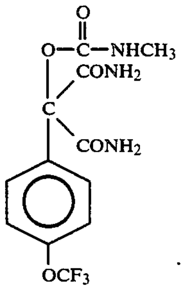
Melting point = 191–192° C.
(14)
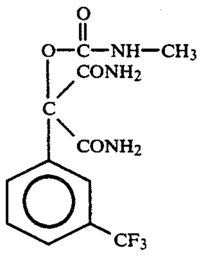
Melting point = 176–177° C.

-continued
(15)
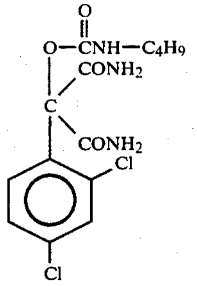
Melting point = 189-191° C.
(16)
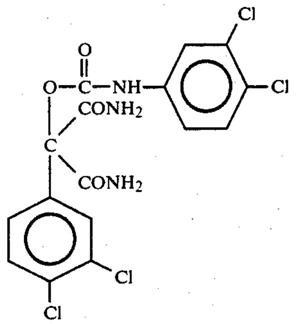
Melting point = 193-194° C.
(17)
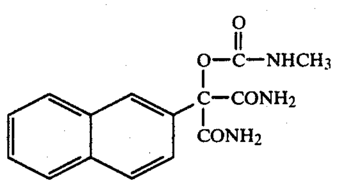
Melting point = 205° C. (decomposition)
(18)
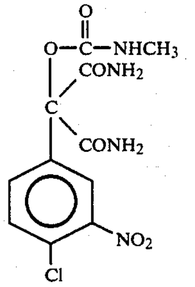
Melting point = 200° C. (decomposition)
(19)
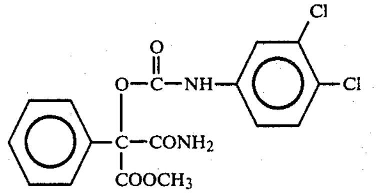
Melting point = 205-208° C.
(19a)
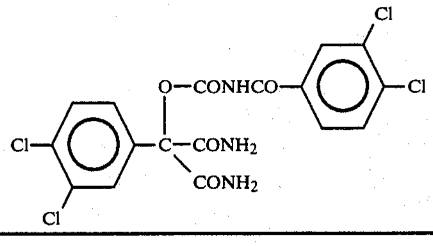
Melting point = 199° C.

Example 20

Process 3

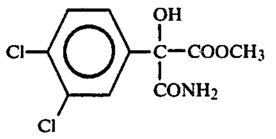

210 g of the ethyl ester of 3,4-dichlorophenyltrimethylsilyloxymalononitrile were added dropwise to 400 g of sulphuric acid (96% strength) at a maximum temperature of 40° C. The mixture was subsequently stirred at room temperature for a further hour and was then stirred into ice-water.

The initially glutinous precipitate, which then crystallises, was taken up in ethyl acetate and the mixture was washed, dried and concentrated.

Recrystallisation from isopropanol gave the methyl ester of 3,4-dichlorophenyl-hydroxy-malonamide of melting point 132°-133° C.

Example 21

Process 3

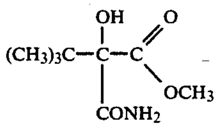

55 g of the methyl ester of tert.-butylhydroxymalonamide were prepared from 187 g of the methyl ester of tert.-butyl-trimethylsilyloxy-malononitrile by hydrolysis in 500 g of $H_2SO_4$ analogously to the above example.

Melting point: 102°-103° C. (from wash benzine).

Example 22

Process 3

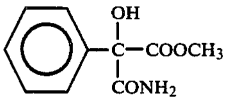

95 g of the methyl ester of phenyl-hydroxy-malononitrile were added dropwise to 500 g of $H_2SO_4$ at 30° C.

After the mixture had been subsequently stirred at room temperature for 30 minutes, it was stirred into ice-water, taken up in methylene chloride, washed and concentrated. The residue was recrystallised from toluene. 72 g of the methyl ester of phenyl-hydroxy-malonamide of melting point 123°-124° C. were obtained.

Example 23

Process 3

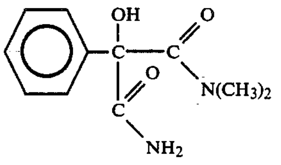

63 g of phenyltrimethylsilyloxymalonic acid dimethylamide-nitrile were added dropwise to 250 ml of concentrated $H_2SO_4$ at 40° C. After the temperature had been kept at 40° C. for 9 hours, with stirring, the mixture was poured onto ice and extracted with $CH_2Cl_2$ and the organic phase was worked up. 31 g of residue remained, and were recrystallised from i-propanol. 26.2 g of phenylhydroxymalonic acid dimethylamide remain; melting point: 137°-138° C.

Example 24

Process 3

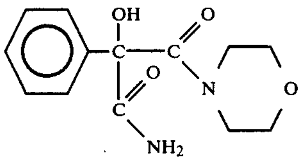

90 g of phenyltrimethylsilyloxymalonic acid morpholide-nitrile were introduced into 300 ml of concentrated $H_2SO_4$ at a maximum temperature of 40° C. After 2.5 hours at 40° C., the mixture was stirred into ice-water and extracted 3 times with methylene chloride. The organic phases were combined, and washed with a little water, and the solvent was distilled off, a high vacuum being applied towards the end. 57 g of a vitreous product which was identified spectroscopically as phenylhydroxymalonic acid morpholide-amide remained.

Example 25

Process 3

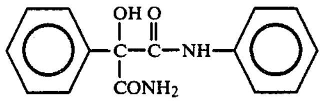

10 g of phenyltrimethylsilyloxymalonic acid anilide-nitrile were introduced into 100 ml of concentrated hydrochloric acid at 30° C. The suspension was then heated at 50° C. for 2 hours, the residue was taken up in methylene chloride and the mixture was washed and worked up. 5 g of a vitreous crude product remained, and were recrystallised from toluene. 4 g of phenylhydroxymalonic acid anilide-amide could be isolated. Melting point: from 110° C., with decomposition.

Example 26

Process 4

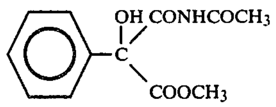

94 g of the methyl ester of phenylhydroxymalononitrile were added dropwise to a solution of 88.6 g of glacial acetic acid and 74 ml of concentrated $H_2SO_4$ at 40°-50° C. After 1 hour, the reaction solution was poured onto ice-water and extracted with methylene chloride. After the organic phase had been worked up, the residue was recrystallised from i-propanol. 50 g of a mixture of the methyl ester of phenylhydroxymalonamide and the methyl ester of phenylhydroxymalonic acid acetylamide in an approximate ratio of 1:1, as was to be ascertained from the spectroscopic data, remained.

Phenylhydroxymalonic acid diamide of melting point 159° C. was obtained by treating the substance mixture with $NH_3$ in methanolic solution at 30°-50° C. for 2 hours.

Example 27

Process 5

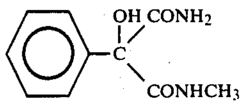

Methylamine was passed into a solution of 42 g of the methyl ester of phenylhydroxymalonamide in 400 ml of methanol at the reflux temperature for 4 hours. After the mixture had been concentrated, 30 g of phenylhydroxy-N-methylamalonic acid diamide (melting point=128° C.) were obtained by recrystallisation from ethanol.

Example 28

Process 5

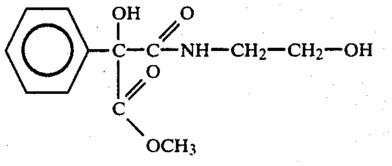

20.9 g of the methyl ester of phenylhydroxymalonamide 6.1 g of ethanolamine and 60 ml of methanol were heated under reflux for 8 hours. After the mixture had been concentrated (under a high vacuum towards the end), 24 g of a highly viscous residue which was identified spectroscopically as the desired phenylhydroxy-N-β-hydroxyethyl-malonic acid diamide, remained.

Example 29

Process 5

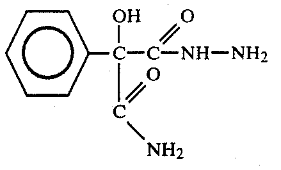

62.7 g of the methyl ester of phenylhydroxymalonamide, 15 g of hydrazine hydrate and 200 ml of methanol were heated under reflux for 4 hours. The mixture was concentrated under a waterpump vacuum up to a bath temperature of 60° C., toluene was added and the mixture was concentrated again, under a high vacuum towards the end. 65 g of a vitreous residue which, by spectroscopy, proved to be phenylhydroxymalonic acid amide-hydrazide, remained.

Example 30

Process 6

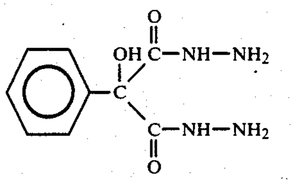

22.4 g of phenylhydroxymalonic acid dimethyl ester and 10 g of hydrazine hydrate in 100 ml of methanol were heated under reflux for 5 hours. The mixture was then concentrated at 50° C., under a high vacuum towards the end. 24 g of a vitreous residue remained and were recrystallised from water. 14 g of phenylhydroxymalonic acid bishydrazide of melting point 159° C. (decomposition) were obtained.

Example 31

Process 6

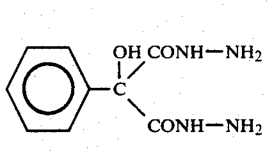

20.9 g of methyl ester of phenylhydroxymalonamide and 25 g of hydrazine hydrate in 150 ml of ethanol were heated under reflux for 12 hours. The mixture was then concentrated and the residue was recrystallised from 75 ml of water. 13 g of phenylhydroxymalonic acid bishydrazide of melting point 159° C. (decomposition remained).

Example 32

Process 6

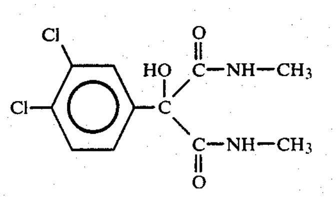

14.7 g of 3,4-dichlorophenylhydroxymalonic acid dimethyl ester were dissolved in 100 ml of methanol, and methylamine was passed in at 60° C. for 1 hour. The mixture was concentrated completely and the crystalline residue was recrystallised from 100 ml of ethanol. 12 g of 3,4-dichlorophenylhydroxymalonic acid dimethylamide (melting point=158°-160° C.) were obtained.

Example 32a 3,4-Dichlorophenylhydroxymalonic acid dineopentylamide (melting point=94°-95° C.) was obtained analogously to the above process.

Example 33

Process 7

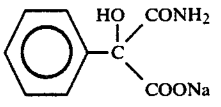

5.41 g of the methyl ester of phenylhydroxymalonamide were stirred with 25.9 ml of aqueous 1N NaOH solution at room temperature for 2.5 hours. The reaction solution thereby became almost homogeneous and the pH value fell to 6. After filtration, the filtrate was concentrated, under a high vacuum towards the end. Ir, NMR and MS (FAB) confirmed the presence of the monosodium salt of phenylhydroxymalonic acid monoamide.

Example 33a

The free acid of the compound of Example 32 was obtained by suspending the salt of Example 33 in methylene chloride and treating the suspension with HCl gas.

Example 34

Process 8

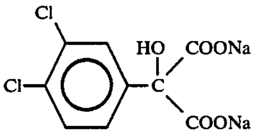

11.2 g of 3,4-dichlorophenylhydroxymalonic acid dimethyl ester were stirred with 76.6 ml of aqueous 1N NaOH solution at room temperature until the solution had a pH value of 6. The solution was then filtered and the filtrate was concentrated.

IR, NRM and MS (FAB) confirmed the presence of the disodium salt of 3,4-dichlorophenylhydroxymalonic acid.

Example 35

Process 9

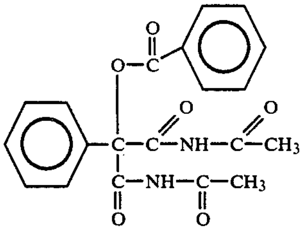

26.5 g of dimeric benzoyl cyanide were added dropwise to a solution of 12 g of glacial acetic acid and 1.5 ml of concentrated $H_2SO_4$ at 75°-80° C. After half an hour, the mixture was poured onto ice and extracted by shaking with methylene chloride and the organic phase was washed and worked up. The residue was recrystallised first from isopropanol and then from ethanol. 10 g of benzoyl-benzoyloxymalonic acid bisacetylamide of melting point 186°-187° C. remained.

Example 36

Process 2a2

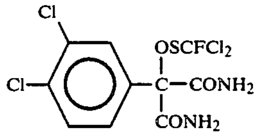

13 g of 3,4-dichlorophenylhydroxymalonic acid diamide and 8.5 g of dichlorofluoromethylsulphonyl chloride in 100 ml of dioxane were heated under reflux for 10 hours. After concentration, 20 g of 3,4-dichlorophenyl-difluoromethylsulphenyloxy-malonic acid diamide of melting point 120° C. (decomposition) remained.

Example 37

Process 10

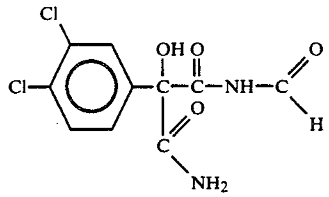

77.3 g of 3,4-dichlorophenyltrimethylsilyloxymalonic acid dinitrile were added dropwise to 67 g of formic acid and 16.8 ml of concentrated $H_2SO_4$ at 25° C. and the mixture was kept at this temperature for 28 hours, with occasional stirring. The mixture was then stirred into ice-water and taken up in ethyl acetate and the organic phase was washed neutral. After working up, 48 g of crude product remained, and were recrystallised from isopropanol. According to spectroscopic investigations (IR, $H^1$— and $C^{13}$—NMR, MS (DCI), 3,4-dichlorophenylhydroxy-N-formyl-malonic acid diamide and 3,4-dichlorophenylhydroxymalonic acid diamide were present in an approximate ratio of 1:1.

Example 38

Process 10

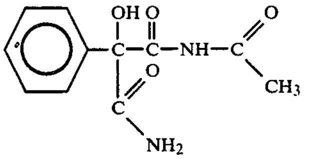

92 g of phenyltrimethylsilyloxymalonic acid dinitrile were added dropwise to a solution of 72 g of glacial acetic acid and 60 ml of concentrated $H_2SO_4$ at 40°-50° C. After 2 hours, the viscous solution was poured onto ice, stirred thoroughly and filtered off with suction. 53 g of crude product remained, and were recrystallised from water. 40 g of phenylhydroxymalonic-N-acetylmalonic acid diamide remained; melting point: 210° C. (decomposition).

Example 38a 3,4-Dichlorophenylhydroxymalonic-N-malonic acid diamide—melting point: 202° C. (decomposition)—was synthesised analogously to the above process.

Example 39

Process 11

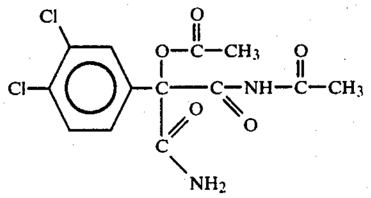

13.2 g of 3,4-dichlorophenylhydroxymalonic acid diamide were heated to 80° C. in 60 ml of acetic anhydride and 6 ml of a solution of 0.3 g of concentrated $H_2SO_4$ in 100 ml of acetic anhydride were added at this temperature. Stirring was continued at 80° C. for 10 minutes, the mixture was then cooled to 20° C. and poured onto ice and the crude product was filtered off with suction. After drying, the product was digested in methylene chloride and filtered off with suction. 8 g of 3,4-dichlorophenyl-acetoxy-N-acetyl-malonic acid diamide of melting point 202° C. (decomposition) remained.

Example 40

Process 11

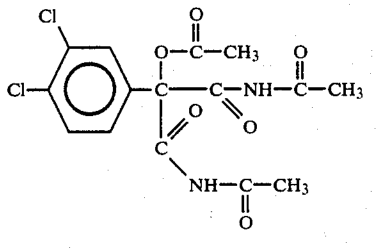

52.6 g of 3,4-dichlorophenylhydroxymalonic acid diamide were suspended in 130 ml of acetic anhydride, and 0.3 ml of concentrated $H_2SO_4$ was added. The mixture was warmed to 80° for 45 minutes, whereupon a clear solution was formed. The crystals which precipitated after cooling were filtered off with high suction and digested with water and a little i-propanol. 55 g of 3,4-dichlorophenyl-acetoxy-malonic acid bisacetylamide of melting point 170° C. remained.

Example 40a 12 g of 4-chloro-3-methylphenylhydroxymalonic acid diamide were reacted analogously to the above example. 14.3 g of 4-chloro-3-methylphenyl-acetoxymalonic acid bisacetylamide of melting point 169°-171° C. were obtained.

Example 41

Process 11

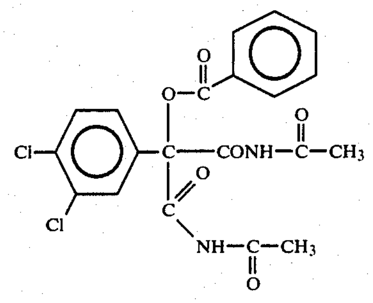

3 drops of concentrated $H_2SO_4$ were added to 7.7 g of 3,4-dichlorophenylbenzoyloxymalonic acid diamide in 60 ml of acetic anhydride and the mixture was heated at 75° C. for 7 hours. It was then poured onto ice-water and filtered off with suction and the product was recrystallised from i-propanol. 4 g of 3,4-dichlorophenylbenzoyloxymalonic acid bisacetylamide of melting point 198° C. (decomposition) were obtained.

Example 42

Process 12

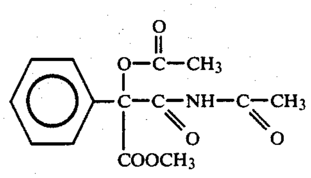

20.9 g of the methyl ester of phenyhydroxymalonamide were dissolved in 150 ml of acetic anhydride at 60° C., and 3 drops of concentrated $H_2SO_4$ were added. The temperature thereby rose to 75° C. The mixture was heated at 80° C. for a further 2 hours and then concentrated, the residue was taken up in toluene and the mixture was washed neutral with water and $NaHCO_3$ solution. After working up, 25 g of an oil, which, according to spectroscopic data, consisted of the methyl ester of phenylacetoxymalonic acid acetylamide, remained.

Example 43

Process 13

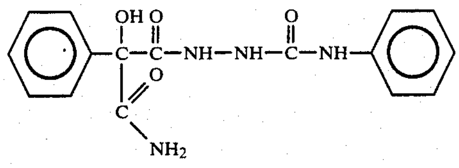

26.4 g of phenylhydroxymalonic acid amide-hydrazide were dissolved in 50 ml of absolute dioxane, and a solution of 15 g of phenyl isocyanate in 15 ml of absolute dioxane was added. The temperature thereby rose to 40° C. and a precipitate separated out. The mixture was filtered cold with suction and the residue was boiled up with 500 ml of water. 27 g of not quite pure phenylhydroxymalonic acid amide-(phenylaminocarbonyl)-hydrazide (melting point: 199° C.) remained.

Example 44

Process 14

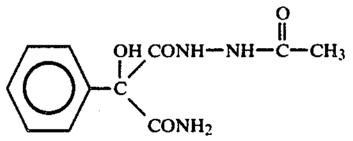

21.2 g of phenylhydroxymalonic acid amide-hydrazide were dissolved in 100 ml of dioxane, 10.3 g of triethylamine were added and 8 g of acetyl chloride were added dropwise. The mixture was subsequently stirred at room temperature for 1 hour, the precipitate was filtered off with suction and the mother liquor was concentrated. Thereafter, 28 g of impure crude product remained, and were taken up in ethyl acetate; the mixture was washed with a little water. After the solvent had been removed under a high vacuum at a bath temperature of 60° C., phenylhydroxymalonic acid amide acetyl hydrazide remained as a vitreous residue.

Example 45

Process 15

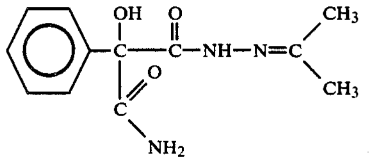

20 g of phenylhydroxymalonic acid amide-hydrazide in 100 ml of acetone were heated under reflux for 3 hours. The crystals were filtered off with suction and recrystallised from ethanol. 15 g of phenylhydroxymalonic acid amide-(2-propylidene)-hydrazide (melting point: 199°-201° C.) were obtained.

Example 46

Process 16

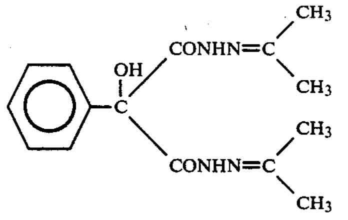

11.2 g of phenlhydroxymalonic acid bishydrazide in 100 ml of acetone was heated under reflux for 4 hours. The mixture was then concentrated, under a high vacuum towards the end. 13.8 g of crude phenylhydroxymalonic acid-bis-(2-propylidene-hydrazide) remained as a highly viscous residue.

Example 47

Process 17

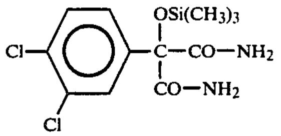

3 g (0.0114 mol) of 3,4-dichloro-phenyl-hydroxymalonic acid diamide, 1.12 g (0.114 mol) of trimethylsilyl cyanide and 0.9 g (0.0114 mol) of pyridine are heated at 100° C. (bath temperature) for 6 hours. After the pyridine has been removed under a waterpump vacuum, the residue is recrystallised from petroleum ether.

3.45 g (90.3% of theory) of 2-(3,4-dichlorophenyl)-2-trimethylsilyloxy-malonic acid diamide of melting point 156° C. are obtained.

Example 48

Process 17

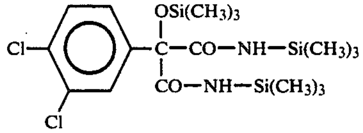

30 g (0.114 mol) of 3,4-dichloro-phenyl-hydroxymalonic acid diamide, 46 g (0.464 mol) of trimethylsilyl cyanide and a few drops of pyridine are mixed and the mixture is heated at the boiling point for 12 hours. After cooling, the mixture is filtered with suction and the residue is washed with a little cold petroleum ether.

48.6 g (89% theory) of 2-(3,4-dichloro-phenyl)-2-trimethylsilyl-1,3-bis-trimethylsilylmalonic acid diamide of melting point 107° to 109° C. are obtained.

The procedure followed was as in the above example, but without pyridine as a catalyst and instead in 130 ml of dioxane as the solvent. After concentration and recrystallisation from wash benzine, the desired end product was also obtained in this case.

The following compounds of the formula (I) can be prepared analogously to Example 48:

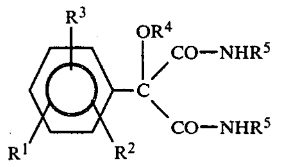

(I)

| Example No. | $R^1$ | $R^2$ | $R^3$ | $R^4$ | $R^5$ | Melting point °C. |
|---|---|---|---|---|---|---|
| 49 | 4-Cl | H | H | $-Si(CH_3)_3$ | $-Si(CH_3)_3$ | 134 |
| 50 | 3-Cl | 5-Cl | H | $-Si(CH_3)_3$ | $-Si(CH_3)_3$ | 112-113 |
| 50a | 3-Cl | 4-Cl | 5-Cl | $-Si(CH_3)_3$ | $-Si(CH_3)_3$ | 236 |

Example 51

Process 17

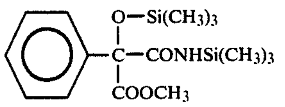

4.2 g of the methyl ester of phenylhydroxymalonamide, 8 g of trimethylsilyl cyanide and 1 drop of pyridine were heated under reflux for 8 hours, the condenser being preheated to 40° C. in order to remove the hydrocyanic acid formed. The mixture was then concentrated at a bath temperature of 40° C., under a high vacuum towards the end. A viscous oil which, according to spectroscopic investigations, consisted of the methyl ester of phenyltrimethylsilyloxymalonic acid trimethylsilylamide, remained.

Example 52

Process 18

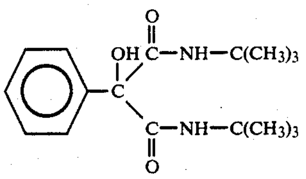

100 g of concentrated sulphuric acid was added dropwise to a solution of 69 g of phenyltrimethylsilyloxymalonic acid dinitrile and 89 g of tert.-butanol in 150 ml of methylene chloride at 0°-5° C. The exothermic reaction was then kept at 40° C. and the mixture was subsequently stirred at 30° C. for a further 30 minutes. The reaction mixture was poured onto ice and extracted by shaking with further methylene chloride. After the crude product (98 g) had been worked up, it was distilled. 89 g of phenylhydroxymalonic acid bis-tert.-butylamide could be obtained. Boiling $point_{0.2}$=116°-118° C., melting point=99°-100° C.

Example 53

Process 19

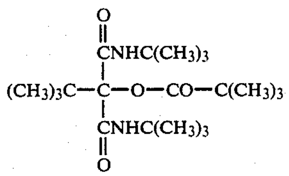

90 g of dimeric pivaloyl cyanide, 120 g of tert.-butanol 150 ml of methylene chloride and 122 g of sulphuric acid were reacted as in Example 52.

136 g of tert.-butyl-O-tert.-butylcarbonyloxymalonic acid bis-tert.-butylamide were isolated. Boiling $point_{0.2}$=105°-106° C.; melting point: 63°-64° C.

Example 54

Process 21

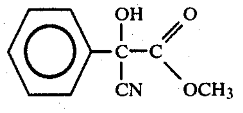

13.5 g of hydrocyanic acid were added dropwise to 82 g of phenylglyoxylic acid methyl ester and 1 ml of triethylamine at 25°-30° C. On the basis of the spectroscopic data, the methyl ester of phenyl-hydroxy-malonomnitrile had formed.

Example 55

Process 21

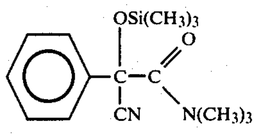

50 g of trimethylsilyl cyanide was added dropwise to 88.5 g of phenylglyoxylic acid dimethylamide and 1 ml of triethylamine at 30° C., with ice-cooling. After 45 minutes, the mixture was degassed under a waterpump vacuum. IR, NMR, MS and GC confirmed the structure of phenyltrimethylsilyoxymalonic acid dimethylamide-nitrile.

Example 56

Phenylglyoxylic acid morpholide was converted into phenyltrimethylsilyloxymalonic acid morpholidenitrile analogously to Example 55.

Example 57

Process 21

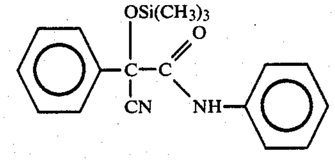

52.3 g of phenylglyoxylic acid anilide were dissolved in 100 ml of absolute methylene chloride, 3 ml of triethylamine were added and 23 g of trimethylsilyl cyanide were added dropwise at a maximum temperature of 30° C. The mixture was subsequently stirred at room temperature for 3 hours and the solvent was then distilled off. The residue was recrystallised from wash benzine; 70 g of phenylfrimethylsilyloxymalonic acid anilide-nitrile of melting point 106°-107° C. were obtained.

EXAMPLE 58

Process 21

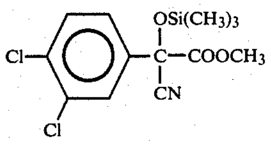

62.8 g of trimethylsilyl chloride were added dropwise to 147.8 g of 3,4-dichlorophenylglyoxylic acid methyl ester and 0.5 ml of triethylamine at a maximum temperature of 55° C., with ice-cooling. 210 g of the methyl ester of 3,4,dichlorophenyl-trimethylsilyloxymalononitrile were obtained. IR, NMR and MS confirm the presence of the substance.

EXAMPLE 59

Process 21

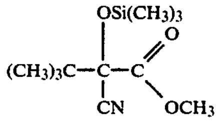

197.8 g of the methyl ester of tert.-butyl-tri-methylsilyloxymalononitrile was prepared from 116.8 g of methylα-keto-3,3-dimethylbutyrate, 0.5 ml of triethylamine and 81 g of trimethylsilyl cyanide.

EXAMPLE 60

Process 23

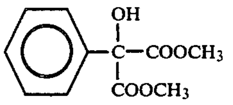

100 ml of absolute methanol were saturated with about 80 g of hydrochloric acid at 10° C. 131.5 g of phenyl-trimethylsilyloxy-malonic acid methylesternitrile was then added dropwise between −10° and −5° C. The homogeneous solution was subsequently stirred at 10°14 15° C. for 1 hour, whereupon it separated into two phases. 9 g of water, diluted with 50 ml of methanol, was then added dropwise and the mixute was subsequently stirred at 20° C. for 2 hours.

The mixture was concentrated, the residue was taken up in methylene chloride, the mixture was washed with water, dried and concentrated and the residue was distilled.

84 g of phenyl-hydroxy-malonic acid bis-methyl ester of boiling point$_{0.5}$=126°-28° C. were obtained.

EXAMPLE 61

Process 23

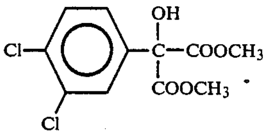

320 ml of absolute methanol were saturated with about 210 g of hydrochloric acid at 10° C. 300 g of 3,4-dichlorophenyl-trimethylsilyloxy-malonic acid dinitrile were added dropwise at −10° C., the mixture was subsequently stirred at 10°-15° C. for 1 hour and 36 g of water, diluted with 50 ml of methanol, were added at 15° C. The mixture was subsequently stirred at a maximum temperature of 30° C. for 1 hour, the crystals which had precipitated were filtered off with suction and the filtrate was concentrated. The residue was taken up in methylene chloride, the mixture was washed with ice-water, dried and concentrated and the residue was distilled. 165 g of 3,4-dichlorophenylhydroxymalonic acid dimethyl ester were obtained. Boiling point$_{0.3}$=154°-58° C.

EXAMPLE 62

Process 21

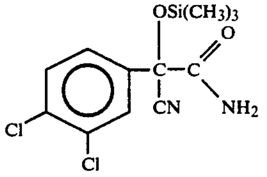

32.7 g of 3,4-dichlorophenylgloyxsylic acid amide were suspended in 100 ml of methylene chloride, 0.2 ml of triethylamine were added and 15 g of trimethylsilyl cyanide were added dropwise. The mixture was subsequently stirred at room temperature for 1 hour and concentrated and the residue was recrystallised from toluene. 41 g of 3,4-dichlorophenyltrimethylsilyloxyamalonic acid amidenitrile were obtained. Melting point: 148°-149° C.

EXAMPLE 62*a*

5 g of the product were stirred in 25 ml conc. sulphuric acid at 25° C. for 1 hour; the solution was poured onto ice and the product was filtered off with suction and washed neutral. 3.2 g of 3,4-dichlorophenylhydroxycarboxylic acid diamide were obtained.

EXAMPLE 63

Process 21

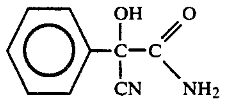

29.8 g of phenylglyoxylic acid amide were suspended in 30 ml of ethylene glycol dimethyl ether, 0.5 ml of triethylamine was added and 5.4 g of hydrocyanic acid were added. A homogeneous solution was formed. After removal of the solvent, phenylhydroxymalonic acid amidenitrile remained.

EXAMPLE A

Plutella test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage Leaves (*Brassica oleracea*) are treated by being dipped into the preparation of active compound of the desired concentration and are infested with caterpillars of the diamond-back moth (*Plutella maculipennis*), as long as the leaves are still moist.

After the specified periods of time, the destruction in % is determined. 100% means that all the caterpillars have been killed; 0% means that none of the caterpillars have been killed.

In this test, for example, the following compounds from the preparation examples show a superior activity compared with the prior art: 37, 38, 38*a*, 4, 39, 40, 5, 36, 3, 2, 41, 16, 10, 19*a*, 1, 47, 50 and 48 .

EXAMPLE B

Tetranychus test (resistant)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, for example, the following compounds from the preparation examples show a superior activity compared with the prior art: 37, 39, 40, 9, 5, 36, 41, 16, 10, 19*a*, 1, 47, 49, 50 and 48.

EXAMPLE C

Test with *Lucilia cuprina* res. Larvae

Emulsifier: 35 parts by weight of ethylene glycol monomethyl ether; 35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the particular desired concentration.

About 20 *Lucilia cuprina* res. Larvae are introduced into a test tube which contains approx. 1 $cm^2$ of horse muscle and 0.5 ml of the preparation of active compound. After 34 hours, the degree of destruction is determined.

In this test, for example, the compound of Example (47) showed 100% destruction at an active compound concentration of 1,000 ppm.

EXAMPLE D

Critical Concentration Test/Root-systemic Action

Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amouont of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l) being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from othe mortality figures. It is 100% if all the test animals have been killed and 0% if just as many test insects are still alive as in the case of the untreated control.

In this test, for example, the following compounds from the preparation examples show a superior action compared with the prior art: 1, 13, 27, 33, 47 and 52.

EXAMPLE E

Critical Concentration Test/Root-systemic Action

Test insect: *Phaedon cochleariae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l) being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all the test animals have been killed and 0% if just as many test insects are still alive as in the case of the untreated control.

In this test, for example, the following compounds from the preparation examples show a superior action compared with the prior art: 49.

EXAMPLE F

Critical Concentration Test/Soil Insects

Test insect: *Phorbia antiqua* (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of the active compound is inimately mixed with soil. The concentration of the active compound in the preparation is of practically no importance, only the amount by weight of active compound per unit volume of soil, which is given in ppm (=mg/l)

being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In the test, for example, the following compounds from the preparation examples show a superior action compared with the prior art: 1, 47, 48, 40, 39, 35 and 38*a*.

We claim:

1. An agent for combating pests, wherein said agent contains a substituted malonic acid derivative of the formula

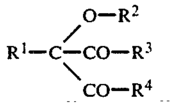

wherein $R^1$ represents phenyl, which is mono-, di- or trisubstituted in the 3-, 4- and 5-positions by identical or different halogen atoms, $R^2$ is hydrogen, $C_{1-4}$-alkyl, optionally halogen-substituted $C_{1-4}$-alkylaminosulphonyl, $C_{1-4}$-alkylcarbonyl, optionally halogen-substituted phenylcarbonyl, phenylsulphenyl, $C_{1-4}$-alkylsulphenyl, trialkylsilyl or

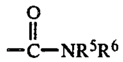

wherein $R^5$ stands for hydrogen and $R^6$ is optionally halogen-substituted phenyl or phenylcarbonyl, or $C_{1-4}$-alkyl or $C_{1-4}$-alkylcarbonyl and $R^3$ and $R^4$ each independently is amino, trimethylsilylamino, formylamino, $C_{1-4}$-alkylcarbonyl-amino, alkylamino, trialkylsilylalkylamino, both radical $R^3$ and $R^4$ only representing amino if $R^2$ is other than hydrogen.

2. A substituted malonic acid derivative of the formula I

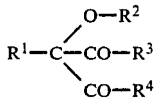

wherein $R^1$ represents phenyl, which is mono-, di- or trisubstituted in the 3-, 4- and 5-positions by identical or different halogen atoms $R^2$ is hydrogen, $C_{1-4}$-alkyl, optionally halogen-substituted $C_{1-4}$-alkylaminosulphonyl, $C_{1-4}$-alkylcarbonyl, optionally halogen-substituted phenylcarbonyl, phenylsulphenyl, $C_{1-4}$-alkylsulphenyl, trialkylsilyl or

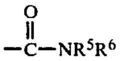

wherein $R^5$ stands for hydrogen and $R^6$ is optionally halogen-substituted phenyl or phenylcarbonyl, or $C_{1-4}$-alkyl or $C_{1-4}$-alkylcarbonyl and $R^3$ and $R^4$ each independently is amino, trimethylsilylamino, formylamino, $C_{1-4}$-alkylcarbonyl-amino, alkylamino, trialkylsilylalkylamino, both radical $R^3$ and $R^4$ only representing amino if $R^2$ is other than hydrogen.

3. A method for combating pests which comprises administering to such pest or to a pest habitat a pesticidally effective amount of a substituted malonic acid derivative of the formula

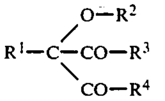

wherein $R^1$ represents phenyl, which is mono-, di- or trisubstituted in the 3-, 4- and 5-positions by identical or different halogen atoms, $R^2$ is hydrogen, $C_{1-4}$-alkyl, optionally halogen-substituted $C_{1-4}$-alkylaminosulphonyl, $C_{1-4}$-alkylcarbonyl, optionally halogen-substituted phenylcarbonyl, phenylsulphenyl, $C_{1-4}$-alkylsulphenyl, trialkylsilyl or

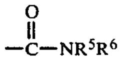

wherein $R^5$ stands for hydrogen and $R^6$ is optionally halogen-substituted phenyl or phenylcarbonyl, or $C_{1-4}$-alkyl or $C_{1-4}$-alkylcarbonyl and $R^3$ and $R^4$ each independently is amino, trimethylsilylamino, formylamino, $C_{1-4}$-alkylcarbonyl-amino, alkylamino, trialkylsilylalkylamino, both radical $R^3$ and $R^4$ only representing amino if $R^2$ is other than hydrogen.

4. An agent according to claim 1 wherein $R^1$ is phenyl substituted by chlorine.

5. A substituted malonic acid derivative according to claim 2 wherein $R^1$ is phenyl substituted by chlorine.

6. A method according to claim 3 wherein in the substituted malonic acid derivative $R^1$ is phenyl substituted by chlorine.

7. A pesticidal composition comprising a diluent and a pesticidally effective amount of a substituted malonic acid derivative according to claim 1.

8. A pesticidal composition comprising a diluent and a pesticidally effective amount of a substituted malonic acid derivative according to claim 5.

* * * * *

CERTIFICATE OF CORRECTION

PATENT NO. : 4,698,333

DATED : Oct. 6, 1987

INVENTOR(S) : Fauss et al.

It is certified that error appears in the above-identified patent and that said Letters Patent is hereby corrected as shown below:

| | |
|---|---|
| Title Page, under U.S. Patent Documents", line 3 | Correct date to --12/72 |
| Col. 3, line 27 | Correct spelling of --trial-kylsilylamino-- |
| Col. 4, line 41 | Correct spelling of --ethylene-dioxy-- |
| Col. 5, line 7 | Correct spelling of --nitrophenyl-- |
| Col. 5, line 12 | Delete "4-4 bromom" and substitute --4-bromo-- |
| Col. 5, line 21 | Correct spelling of --tribromophenyl-- |
| Col. 6, line 16 | Correct spelling of --alkylsilyl-amino-- |
| Col. 7, line 10 | Correct spelling of --trimethylsilyl-- |
| Col. 7, line 22 | Correct spelling of --trimethylsily-lamino-- |
| Col. 7, line 22 | Correct spelling of --alkylcarbony-lamino-- |
| Col. 7, line 31 | Correct spelling of --trimethylsilyl-- |
| Col. 9, line 68 | Insert --with-- after "or" in the first instance |
| Col. 10, line 3 | Insert --)-- after "(above" |
| Col. 19, line 43 | Delete formula |
| Col. 20, line 26 | Correct spelling of --inorganic-- |
| Col. 21, line 51 | Correct spelling of --described-- |
| Col. 22, line 29 | Correct spelling of --halogenated-- |
| Col. 22, line 64 | Correct spelling of --preferably-- |
| Col. 23, line 32 | Insert --may-- before "also" |

UNITED STATES PATENT AND TRADEMARK OFFICE
CERTIFICATE OF CORRECTION

PATENT NO. : 4,698,333
DATED : Oct. 6, 1987
INVENTOR(S) : Fauss et al.

It is certified that error appears in the above-identified patent and that said Letters Patent is hereby corrected as shown below:

| | |
|---|---|
| Col. 25, line 2 | Delete "4-chlora-3-methylaniline" in the third instance |
| Col. 25, line 8 | Correct spelling of --dichloro-- |
| Col. 26, line 41 | Correct spelling of --substituent-- |
| Col. 27, line 8 | Correct spelling of "The" in the first instance |
| Col. 28, line 14 | Correct spelling of --dichlorobenzene-- |
| Col. 32, line 63 | Correct spelling of --compounds-- |
| Col. 34, line 15 | Correct spelling of --prepared-- |
| Col. 36, line 44 | Correct spelling of --customary-- |
| Col. 37, line 63 | Delete "XLII" and substitute --XLVII-- |
| Col. 39, line 25 | Delete "Derivative" and substitute --Derivate-- |
| Col. 40, line 68 | Correct spelling of --Dermaptera-- |
| Col. 41, line 10 | Correct spelling of --intermedius-- |
| Col. 41, line 45 | Correct spelling of --Attagenus-- in second instance |
| Col. 44, line 17 | Delete "1NCl" and substitute --1 N HCl-- |
| Col. 55, line 16 | Delete "Ir" and substitute --IR-- |
| Col. 57, line 4 | Insert --acetyl-- after "-N-" |
| Col. 62, line 14 | Correct spelling of --malononitrile-- |
| Col. 63, line 36 | Delete "14" and substitute -- - -- |
| Col. 64, line 16 | Correct spelling of --dichlorophenylglyoxylic-- |

UNITED STATES PATENT AND TRADEMARK OFFICE

CERTIFICATE OF CORRECTION

PATENT NO. : 4,698,333

DATED : Oct. 6, 1987

INVENTOR(S) : Fauss et al.

It is certified that error appears in the above-identified patent and that said Letters Patent is hereby corrected as shown below:

Col. 64, line 23 Delete "yamalonic" and substitute --ymalonic--

Signed and Sealed this

Twenty-fourth Day of May, 1988

*Attest:*

DONALD J. QUIGG

*Attesting Officer* *Commissioner of Patents and Trademarks*